United States Patent [19]

Igarashi et al.

[11] Patent Number: 5,466,716
[45] Date of Patent: * Nov. 14, 1995

[54] LIPOSOMAL TRIMETHYLSPHINGOSINE

[75] Inventors: Yasuyuki Igarashi; Mohammad N. Ahmad; Hirofumi Okoshi; Sen-itroh Hakomori, all of Seattle, Wash.

[73] Assignee: The Biomembrane Institute, Seattle, Wash.

[*] Notice: The portion of the term of this patent subsequent to Aug. 11, 2009, has been disclaimed.

[21] Appl. No.: 221,788

[22] Filed: Apr. 1, 1994

Related U.S. Application Data

[63] Continuation-in-part of Ser. No. 81,383, Jun. 30, 1993, Pat. No. 5,331,014, which is a continuation-in-part of Ser. No. 724,625, Jul. 2, 1991, Pat. No. 5,151,360, which is a continuation-in-part of Ser. No. 636,353, Dec. 31, 1990, Pat. No. 5,137,919.

[51] Int. Cl.⁶ .......................... A61K 47/00; A61K 31/14
[52] U.S. Cl. ............................................ 514/642; 424/121
[58] Field of Search ............................ 514/642; 424/1.21

[56] References Cited

U.S. PATENT DOCUMENTS

| | | | |
|---|---|---|---|
| 5,137,919 | 9/1992 | Igarashi et al. | 514/642 |
| 5,151,360 | 9/1992 | Handa et al. | 435/240.2 |
| 5,248,824 | 9/1993 | Igarashi et al. | 564/292 |

*Primary Examiner*—Richard L. Raymond
*Attorney, Agent, or Firm*—Sughrue, Mion, Zinn, Macpeak & Seas

[57] ABSTRACT

Liposomal N,N,N-Trimethylsphingosine and pharmaceutical compositions comprising same.

4 Claims, 16 Drawing Sheets

Sphingosine (1) X=H
N.N-Dimethylsphingosine (2) X=Me

N.N.N-Trimethylsphingosine (3)

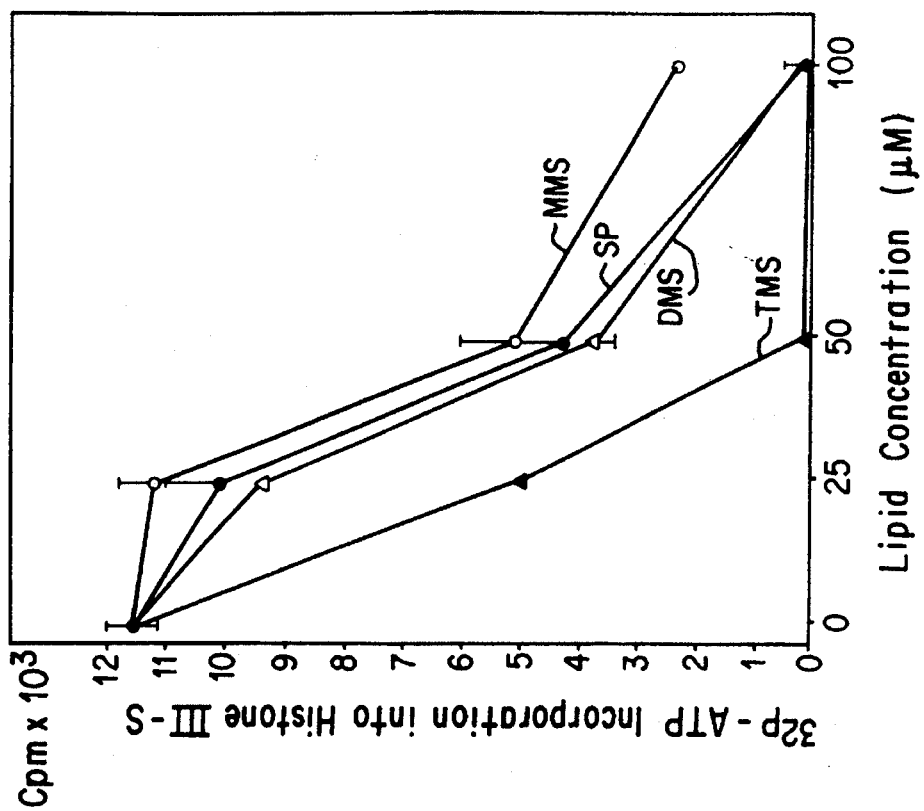
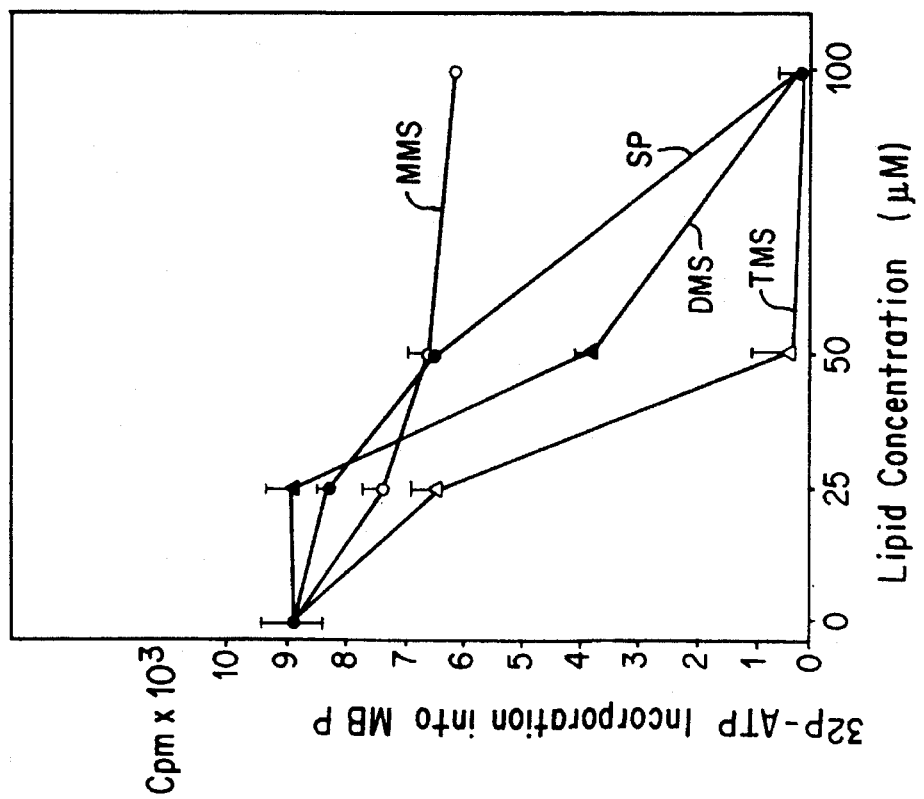
FIG. 4B
FIG. 4A

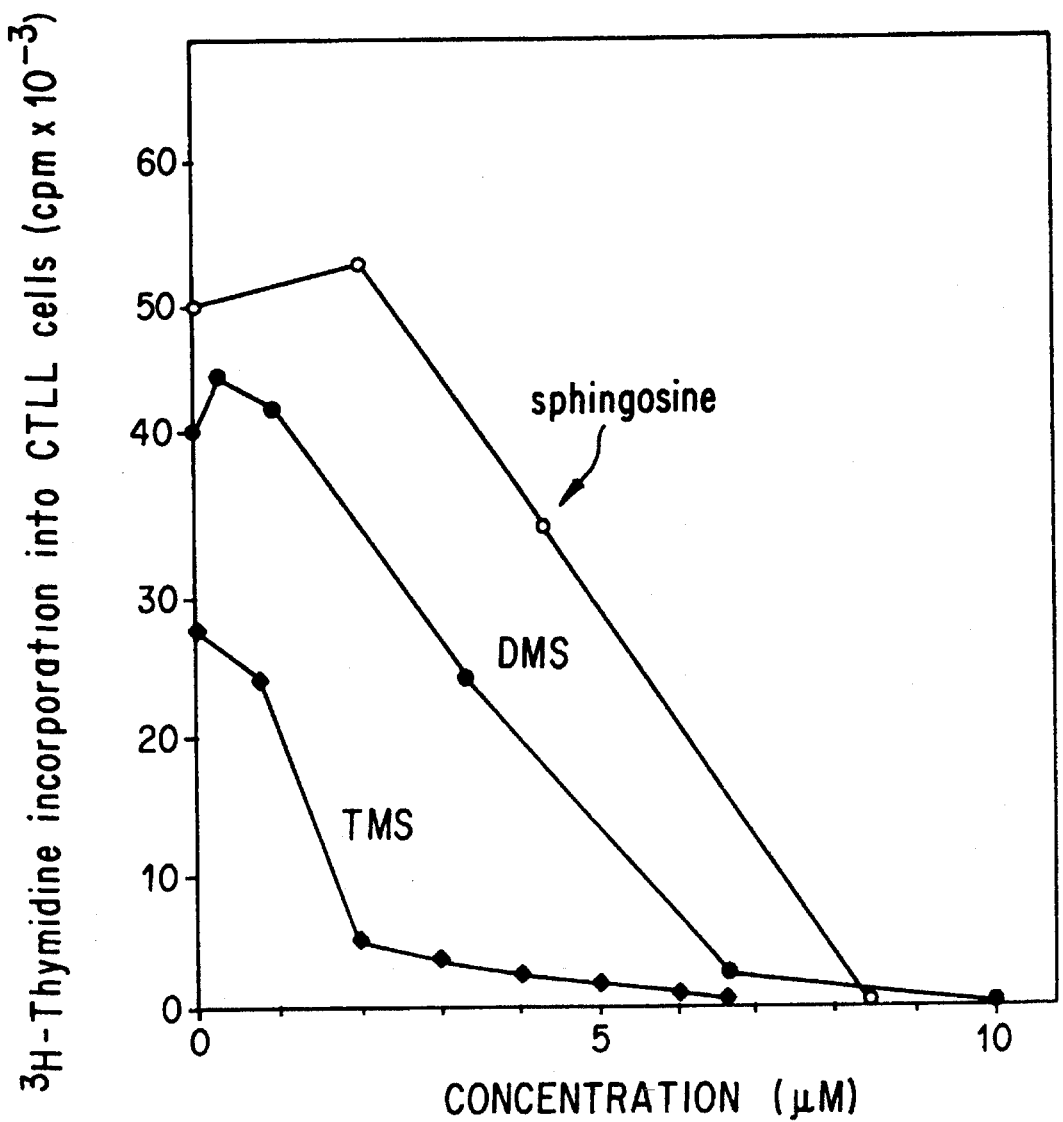
F I G. 10

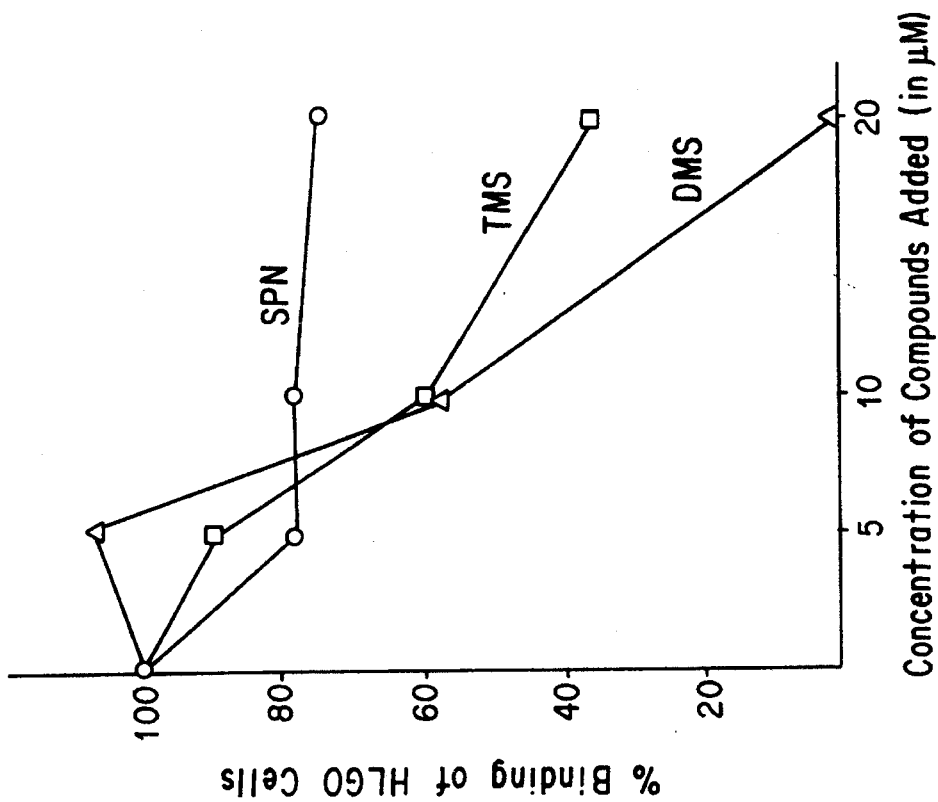
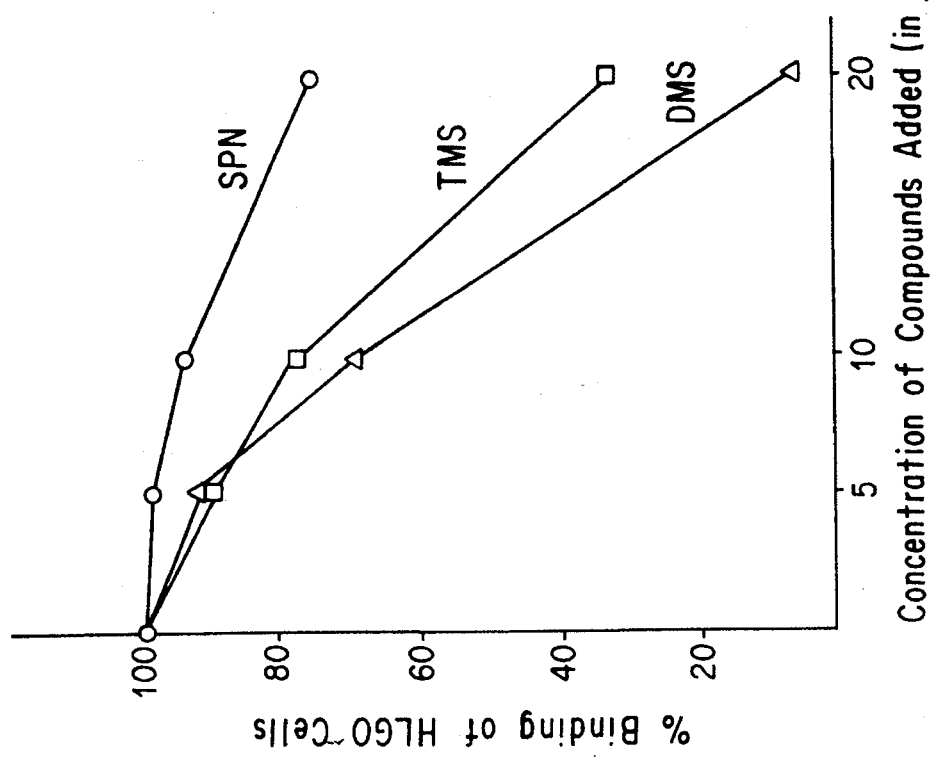
FIG. 12B
FIG. 12A

LIPOSOMAL TRIMETHYLSPHINGOSINE

Portions of the research disclosed herein were supported in part by the National Cancer Institute. This application is a continuation-in-part application of application U.S. Ser. No. 08/081,383 filed 30 Jun. 1993, now U.S. Pat. No. 5,331,014, which is a continuation-in-part application of U.S. Ser. No. 07/724,625 filed 2 Jul. 1991, now U.S. Pat. No. 5,151,360, which is a continuation-in-past application of application U.S. Ser. No. 07/636,353 filed 31 Dec. 1990, now U.S. Pat. No. 5,137,919.

FIELD OF THE INVENTION

The invention relates to compounds with a profound effect on protein kinase-C activity and mammalian cell proliferation; and methods of using the same.

BACKGROUND OF THE INVENTION

Sphingosine (SPN) is a long chain unsaturated amino alcohol of the formula $C_{18}H_{37}O_2N$ found in cell membranes and in high concentration in nervous tissue. Sphingosine and sphingoid base (a long chain aliphatic base comprising a 1,3-dihydroxy-2-amino group at a terminus and derivatives thereof) have been implicated as inhibitors of protein kinase-C (PK-C) and EGF receptor-associated tyrosine kinase (EGF-RK) (Hannun & Bell, Science, 235, 670, 1987; Hannun, JBC, 261, 12604, 1986; Kreutter et al., JBC, 262, 1632, 1987).

Protein kinase-C activity is related closely to cell growth and recent studies indicate that increased tumorigenicity is correlated with over expression of $PK-C_{\beta 1}$ and $PK-C_{\gamma}$ in some experimental tumors (Housey et al., Cell, 52, 343, 1988; Persons et al., Cell, 52, 447, 1988). A mutant $PK-C_\alpha$ induces highly malignant tumor cells with increased metastatic potential (Megidish & Mazurek, Nature, 324, 807, 1989). It would appear that aberrant expression of PK-C may relate to tumor progression.

Recent studies indicate that phospholipids, sphingolipids and metabolic products thereof have an important role in the modulation of transmembrane signaling through PK-C and other membrane-associated kinases, such as EGF receptor-associated tyrosine kinase (Hakomori, JBC, 265, 18713, 1990). For example, PK-C activity is promoted by diacyl glycerol and inhibited by sphingosine (Hannun & Bell, supra; Hannun & Bell, Science, 243, 500, 1989; Merrill & Stevens, Biochem. Biophys. Acta, 1010, 131, 1989).

Sphingosine did not inhibit PK-C in vitro or at concentrations below 100 µM and did not exhibit a stereospecific effect on Pk-C ((Igarashi et al., Biochem., 28, 6796, 1989). Many of the studies described above employed sphingosine obtained from a commercial source (for example Sigma Chemical Company) and the preparations contained various impurities including 3-O-methylsphingosine, 5-O-methyl-spingosine and N-methylsphingosine. The impurities are likely to result from the process of preparation, namely methanolysis of sphingosine backbone, the D-erythro configuration about the chiral carbons is often converted to the D-threo configuration.

Igarashi et al. (supra) found that the inhibitory effect of sphingosine of PK-C activity is due to: (1) the stereospecific configuration of C2 to C3 (D-erythro configuration required); (2) presence of a long-chain aliphatic group; and (3) perhaps most essential, a negative charge at the primary amino group at C2. If the amino group was N-acetylated, the PK-C inhibitory activity was abolished since the negative charge of an amino group was eliminated by acetylation. However if the anionic character of the amino group was enhanced by N-methylation, the stereospecific PK-C inhibitory activity was enhanced.

Interaction of leukocytes with activated platelets and endothelial cells is an initial step in inflammatory processes and is mediated in part by a family of adhesion molecules known as selectins. Selectins include MEL-14 in mouse and ELAM-1, LAM-1 and GMP-140 (CD62/PADGEM) in man. The selectins are characterized by a similar structural motif consisting of a lectin domain at the N-terminal region, followed by an epidermal growth factor sequence, a complement-regulatory domain, a transmembrane region and a C-terminal domain (Stoolman, Cell, 56, 907, 1989 and Osborn, Cell, 62, 3, 1990). Members of the selectin family bind carbohydrate ligands (see for example, Springer, Nature, 346, 425, 1990; Brandley et al., Cell 63, 861, 1990; Lowe et al., Cell, 63, 475, 1990; and Walz et al., Science, 250, 1132, 1990).

Based on inhibition studies using a variety of glycosphingolipid liposomes, the binding epitopes of both ELAM-1 and GMP-140 expressed on HL60 (a human promyelocytic cell line) cells were identified as sialosyl-$Le^x$ (Phillips et al., Science, 250, 1130, 1990 and Polley et al., Proc. Natl. Acad. Sci., 1991, in press).

Expression of selectins is up-regulated by the inductive effect of lymphokines, tumor necrosis factor (TNFα), bacterial lipopolysaccharides phorbol esters, thrombin and perhaps many other compounds. Leukocytes, together with platelets, thereby are recruited to the inflammatory site. Since tumor cells are capable of activating platelets (see for example, Ugen et al., J. Natl. Canc. Inst., 80, 1461, 1988; Watanabe et al., Canc. Res., 48, 6411, 1988; and Grignani & Jamieson, Blood, 71, 844, 1988), a similar process can be expected to occur during tumor cell adhesion on microvascular endothelia. Thus, the process of tumor cell metastasis may be initiated by selectin-dependent tumor cell adhesion. Although there is no evidence of direct activation of endothelial cells by tumor cells, IL-1 or TNFα-activated endothelial cells have been shown to adhere to a variety of tumor cells (Walz et al., supra).

While the regulatory mechanism for expression of selectins is understood poorly, it apparently involves a complex sequence of transmembrane signaling transducers including protein kinase-C, members of the G-protein family (for example, ras, $G_s$, $G_i$, $G_0$ etc.) and a 47 kDa phosphoprotein, all of which have been shown to be modulated by glycosphingolipids and sphingosine derivatives. Platelet aggregation and associated ATP secretion are inhibited strongly by trimethylsphingosine (TMS). The phenomenon could result from inhibition of 47 kDa protein phosphorylation or of phosphoinositide turnover as a membrane signaling pathway in platelets.

TMS has a quaternary ammonium structure and displays excellent solubility in aqueous solvents. Although there is no clear evidence that TMS is present or has a role in normal cells, synthetically prepared TMS has lower cytotoxicity and stronger pharmacologic effects on, for example, tumor cells and platelets. Thus, TMS offers advantages over the use of SPN or dimethylsphingosine (DMS) in uses wherein the effect is responsive to sphingoid derivatives.

SUMMARY OF THE INVENTION

One object of the invention is to provide a compound and composition for inhibiting metastatic properties of malignant tumor cells, for controlling cell proliferation and for treating various disorders characterized by abnormal cell proliferation.

Another object of the invention is to provide a compound and composition which inhibits protein kinase-C.

A further object of the invention is to provide a compound and composition for inhibiting platelet aggregation.

A fourth object of the invention is to provide a compound and composition for inhibiting inflammation.

Another object of the invention is to provide a method for making N,N,N-trimethylsphingosine.

A sixth object of the invention is to provide a medicament and method of treating malignancy and inhibiting metastatic properties of malignant tumor cells.

A seventh object of the invention is to provide a compound for modulating cell adhesion molecule expression.

An eighth object of the invention is to provide a compound for treating thrombosis.

A ninth object of the instant invention is to provide a method for modulating neutrophil activity.

A tenth object of the instant invention is to provide a method for minimizing tissue damage.

Another object of the instant invention is to provide a method for minimizing the deleterious effects of superoxide.

A yet further object of the instant invention is to provide a method for preserving or prolonging the preservation of biologic materials.

The and other objects have been attained by the development of a method for making N,N,N-trimethylsphingosine and observations in vitro and in vivo of its efficacy in controlling cell proliferation and inhibiting malignant phenotypes of tumor cells.

It has been found that N,N,N-trimethylsphingosine has a higher inhibitory activity on protein kinase-C and metastatic potential of tumor cells than other sphingosine derivatives; inhibits platelet aggregation and tumor-induced platelet interaction; inhibits inflammatory processes; affects the expression of intercellular adhesion molecules and is water soluble. A striking depression of tumor cell metastasis by N,N,N-trimethylsphingosine could be due to its inhibitory activity on protein kinase-C or on platelet aggregation or on both. TMS also inhibited superoxide ($O_2^-$) production, as measured by cytochrome C reduction (Superoxide is a highly reactive molecule that can have deleterious biologic effects. Thus, TMS can minimize tissue damage by inhibiting superoxide production.), $O_2$ consumption, phagokinesis, trans-endothelial migration, 12-myristate 13-acetate (PMA)-induced protein phosphorylation, particularly of proteins with Mr's of about 65 kDa and 47 kDa, both of which could be effected via PKC and formyl-methionyl-leucyl-phenylalanine (fMLP)-dependent turnover change in phosphoinositides.

BRIEF DESCRIPTION OF THE DRAWINGS

In FIG. 2A the growth of human colonic cancer cell line COLO-205 was monitored. In FIG. 2B the growth of human lung cancer cell line LU-65 was monitored. In FIG. 2C the growth of human gastric cancer cell line MKN-74 was monitored. In each Figure the ordinate represents the percent inhibition of tritiated thymidine incorporation, the solid circles represent sphingosine, the open circles represent N,N-dimethylsphingosine and the triangles represent N,N,N-trimethylsphingosine.

FIGS. 4A and 4B depict the effect of sphingosine derivatives on protein kinase-C activity in A431 cells. The standard liposome method of Kraft and Anderson (Nature 301, 621, 1983) was used. In FIG. 4A the ordinate shows the amount of $^{32}$p-ATP that was incorporated into myelin basic protein. In FIG. 4B radioactive incorporation into histone III-s is depicted on the ordinate. In both panels SP represents sphingosine, MMS represents N-monomethylsphingosine, DMS represents N,N-dimethylsphingosine and TMS represents N,N,N-trimethylsphingosine.

In FIG. 6A the open bars depict the total number of lung colony deposits; the stippled bars depict the number of lung colonies with a diameter of greater than 1 mm; and the solid bars depict the number of lung colonies with a diameter of less than 1 mm. Bars 1–3 depict the number of deposits observed 14 days after injection. Bars 4–6 depict the number of lung colony deposits in animals that received BL6 cells and 1 minute later received 0.2 mg of N,N,N-trimethylsphingosine (TMS). Bars 7–9 depict the number of lung colony deposits in animals that received BL6 cells and 0.2 mg of TMS simultaneously. Bars 10–12 depict the number of deposits in animals that received TMS three hours after administration of BL6.

In FIG. 6B the number of lung colonies was determined 16 days after treatment, the treatment consisting of varying doses and routes of administration. Bar 1: $3 \times 10^4$ BL6 cells i.v. Bar 2: $5 \times 10^6$ BL6 cells s.c. Bar 3: $3 \times 10^4$ BL6 cells i.v. with 0.5 mg TMS i.p. one hour later. Bar 4: $5 \times 10^6$ BL6 cells s.c. with 0.5 mg sphingosine i.v. one hour later. Bar 5: $5 \times 10^6$ BL6 cells s.c. with three doses of 0.5 mg TMS i.v. 2, 3 and 4 days later.

In FIG. 6C the dose responsiveness of BL6 metastatic potential to TMS is presented. Bar 1 depicts a control comprising colony numbers in lungs of animals wherein $4 \times 10^4$ BL6 cells in PBS were injected i.v. Bar 2 depicts the number of colonies in lungs of animals that received 0.1 mg of TMS in 100 µl PBS, 1 minute after injection of BL6 cells. Bar 3 represents animals treated in the same manner except that the dose of TMS was doubled to 0.2 mg. Bar 4 represents animals that were treated similarly but with 0.5 mg of TMS. Bar 5 represents animals that first were injected with 0.5 mg of TMS in PBS and 1 minute later were injected with $4 \times 10^4$ BL6 cells in 100 µl of PBS. Sixteen days after treatment, the mice were sacrificed, lungs opened and the number of colonies in the lungs were counted under a dissecting microscope.

FIG. 10 depicts the effect of sphingosine derivatives on mouse T-cell line CTLL. Each point is the mean of three replicates. In the figure DMS represents N,N-dimethylsphingosine and TMS represents N,N,N-trimethylsphingosine.

FIGS. 12A and 12B depict results of representative experiments assessing the degree of HL60 binding to platelets. Platelets were exposed to inhibiting compounds (symbols are the same as in the legend to FIGS. 11A and 11B) and affixed to the wells of a microtiter plate. HL60 cells labelled with tritiated thymidine were introduced into the wells and the amount of bound radioactivity was assessed.

In FIG. 13A, the effect of TMS on $O_2$ production was determined by monitoring the superoxide-mediated reduction of cytochrome C (Clifford, Meth. Enz., 105, 393, 1981) by $10^6$ neutrophils/ml at $OD_{550}$ and an extinction coefficient of 21000/M/cm in a Beckman DU-50 spectrophotometer. The cells were preincubated for 10 minutes at room temperature with the noted concentrations of TMS prior to stimulation with 1 µM PMA (time 0). In FIG. 13B, it is noted that oxydradical production was inhibited immediately upon exposure to 15 µM TMS.

DETAILED DESCRIPTION OF THE INVENTION

Figure 1:
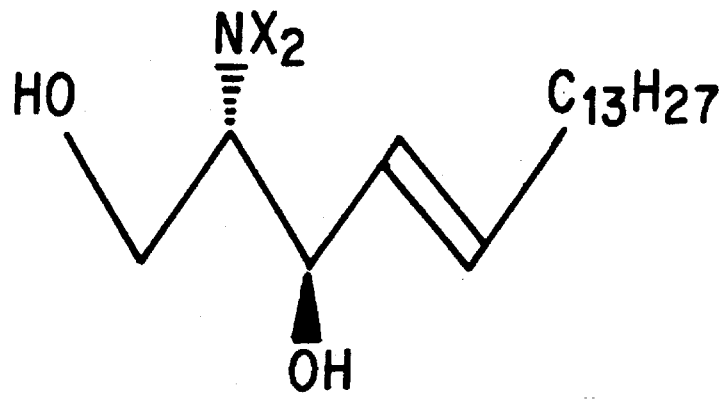
FIG. 1 depicts the structure of N,N,N-trimethylsphingosine and related compounds.
Figure 1:
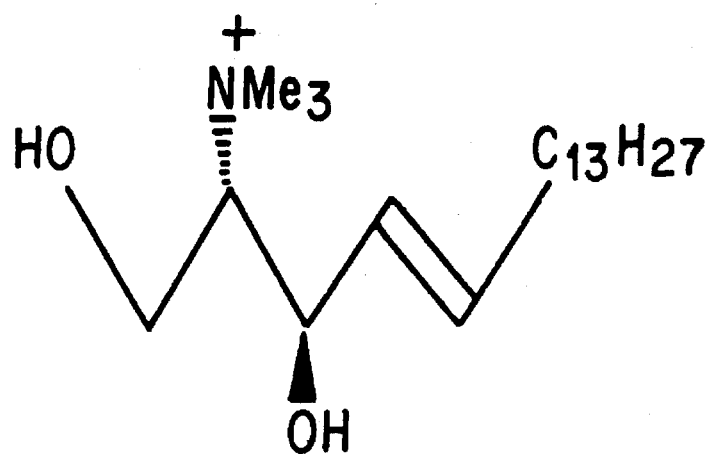

N,N,N-trimethylsphingosine (TMS) is highly water soluble, particularly at physiologic pH. Thus the compound has a distinct advantage over sphingosine, N-monomethylsphingosine and N,N-dimethylsphingosine, which are less water soluble, as a modulator of cell proliferation.

As used herein, sphingosine indicates sphingosine irrespective of D- or L- erythro- or threo- configuration.

Also as used herein, "cells" include nucleated and anucleated structures. Thus, in addition to the 'classical' cells, such as lymphocytes and endothelial cells, biologic structures such as erythrocytes and platelets fall within the ambit of the term.

As used herein, blood or blood products includes whole blood, blood cell preparations, such as packed leukocytes or packed platelets, and the like, outside of the body.

Further as used herein, "synthetically prepared" means a product prepared from commercially available reagents and building blocks and assembled into sphingosine and derivatives thereof by chemical reaction in vitro. Otherwise, sphingosines are prepared from sphingolipids which occur naturally.

Because of the multi-fuctionalized nature of the parent molecule, sphingosine, direct quaternization by exhaustive methylation (Sommer et al., J. Org. Chem. 36, 824, 1971) or reductive methylation using aqueous formaldehyde ($CH_2O$/$NaBH_3$) is not always reproducible. Alternatively, N,N,N-trimethylsphingosine can be prepared synthetically from commercially available unsubstituted reagents. For example, unsubstituted sphingosine (Sigma Chemical Company) can be derivatized to form the compound, (4E)-N,N-dimethyl-D-erythro-sphingosine, by a known method (Igarashi et al. JBC, 265, 5385, 1990). The N,N-dimethylsphingosine so obtained undergoes quaternization in almost quantitative yield.

Briefly, about a 37% aqueous solution of formaldehyde (which is about 20 eq.) is added to a solution of D-erythrosphingenine in acetate buffer ($NaOAc-AcOH-H_2O$, pH 4.5). The solution is mixed at room temperature for about 10 minutes and then sodium cyanoborohydride ($NaCNBH_3$) is added three times (at about 3.0, 2.0 and 1.0 eq., respectively). Excess methanol is added sequentially at five minute intervals. The solution is concentrated under a nitrogen stream in an "N-EVAP" (Organomation Assoc., Inc., South Berlin, Mass.) and the compound extracted with chloroform. When the quantity is large (that is more than about 5–10 mg), the solutio is recommended to further concentration under reduced pressure in a rotary evaporator.

The extract can be purified by high pressure thin layer chromatography using standard procedures. By that technique the compound has an $R_f$ of about 0.6 in a buffer comprising $CHCl_3$:MeOH:$NH_4OH$ in a ratio of 8:2:0.2 by volume.

N,N-dimethylsphingosine prepared as described above was obtained as a colorless syrup in about 80% yield. The molecule has a formula weight of 329.3281 with a formula of $C_{20}H_{40}HNO_2$ as deduced from high resolution mass spectrometry.

Then about 30 milligrams (0.091 m/mol) of (4E)-N,N-dimethyl-D-erythro-sphingosine (DMS) are dissolved in about 1.5 ml of anhydrous chloroform. Freshly distilled iodomethane (a volume of about 170 μl, 2.73 m/mol) is added to the DMS solution and the mixture is stirred in the dark at ambient temperature. (The amount of excess iodomethane is not critical and amounts from 25 to 100% in excess produce satisfactory results.)

The reaction generally is complete in a few hours, although for convenience the mixture is allowed to stand overnight. Progress of the reaction can be monitored by thin layer chromatography (TLC) using a buffer comprising ethyl acetate:methanol:ammonium hydroxide in a ratio of 20:10:2. After incubation, the precipitated quaternary ammonium salt is diluted with water and then repeatedly extracted with chloroform (3 ml×4). The organic layer is dried over magnesium sulphate and then concentrated in vacuo.

Practicing the above method, 37 mg (86% yield) of compound was obtained as yellow crystals.

The yellow crystals are dissolved with stirring in an aqueous suspension of preneutralized (pH=7.00) anion exchange resin (chloride form, Dowex 1×2-400, 500 mg) at room temperature for three hours. The mixture then is filtered through a sintered glass funnel and then freeze dried (8 millitorr for two days).

Practicing the above method, 26.5 mg (93% yield) of N,N,N-trimethylsphingosine chloride salt was obtained. the structure of the product was ascertained by proton nuclear magnetic resonance (500 MHz, CDCl$_3$) and found to contain nine hydrogen groups and a trimethyl derivatized amino group. $^1$H-NMR (D$_2$O) δ 0.88 (t, 3, J=6.8 Hz, Me), 1.31 (br s, 22, 11×CH$_2$), 2.08 (q, 2, J=6.8 Hz, 2×H-6), 3.29 (s, 9 N$^+$Me$_3$), 3.38 (br s, 1, H-3), 4.13 (br s, 2, 2×H-1), 5.57 (dd, 1, J=3.1 and 3.4 Hz, H-4), and 5.90 (m, 1, H-5). The predicted molecular formula of the compound is $C_{21}H_{44}NO_2$ with an expected molecular weight of 342.3372 and mass spectroscopy reveals a formula weight of 342.3371 ($C_{21}H_{44}NO_2$, Δ-0.0003).

The effect of TMS on cell proliferation can be demonstrated in part by exposing various tumor cells to the compound in vitro and in vivo. For comparison purposes those same test cells also are exposed to sphingosine and N,N-dimethylsphingosine. A ready advantage of TMS over the other two compounds is the water solubility thereof. N,N-dimethylsphingosine and sphingosine are soluble in water as chloride salts and at slightly acidic pH. At neutral or physiologic pH, those solutions tend to form opaque suspensions. TMS in soluble under acidic, neutral or basic conditions providing stable, clear solutions.

An in vitro assay relying on tritiated thymidine incorporation can be used to ascertain the effect of various compounds on cell proliferation. Briefly, tumor cells are seeded in flat bottom 96 well plates (Corning, N.Y.) at a concentration of 2×10$^4$ cells per well. The cells are cultured for 2 days in DMEM containing various concentrations of sphingoid, which is added as a PBS solution. The medium then is supplemented with tritiated thymidine at a concentration of 0.5 μCi per well. Following a six hour incubation the cells are collected using the PHD Cell Harvester (Cambridge Technology, Cambridge, Mass.) and amounts of incorporated radioactivity are determined after adding a suitable cell lysing agent and scintillation cocktail, such as ScintiVerse BD (Fisher Scientific, Fairlawn, Calif.) which performs both functions.

Three cancer cell lines were examined, Colo-205, a human colon cancer line (ATCC No. CCL 222); Lu-65, a lung cancer cell line (T. Yamada et al., Jpn, J. Cancer Res., 76, 967–976 (1985); and MKN-74, a gastric cancer cell line (Motoyama et al., Acta Med. Biol., 27, 49–63 (1979).

Figure 2C:
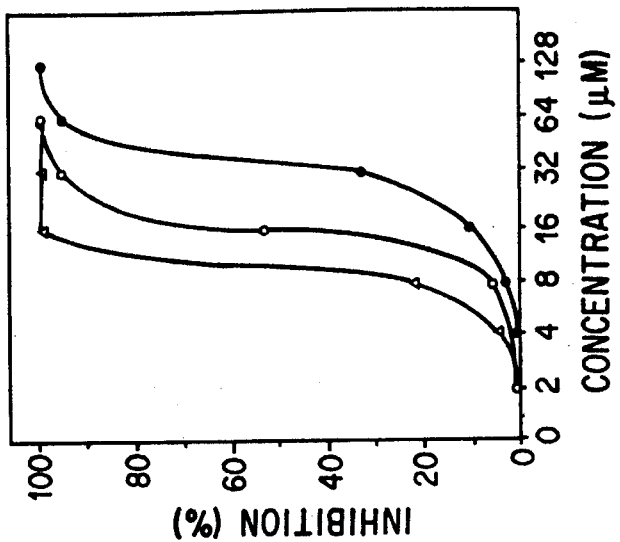
FIGS. 2A–2C show the effect of sphingosine derivatives on human tumor cell growth.
Figure 2B:
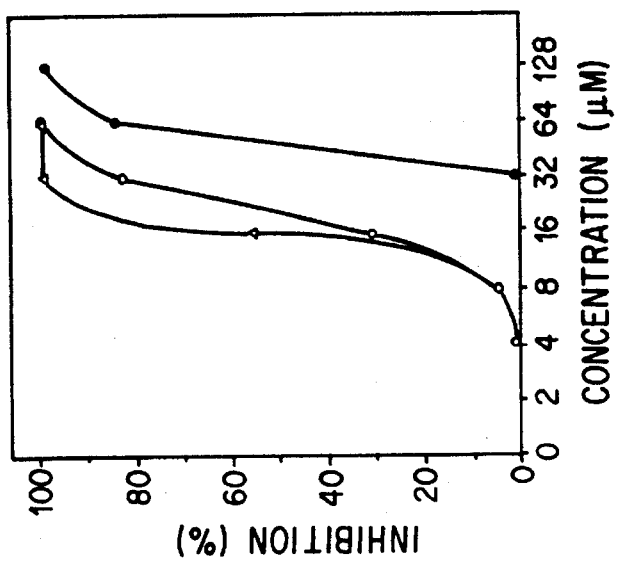
Figure 2A:
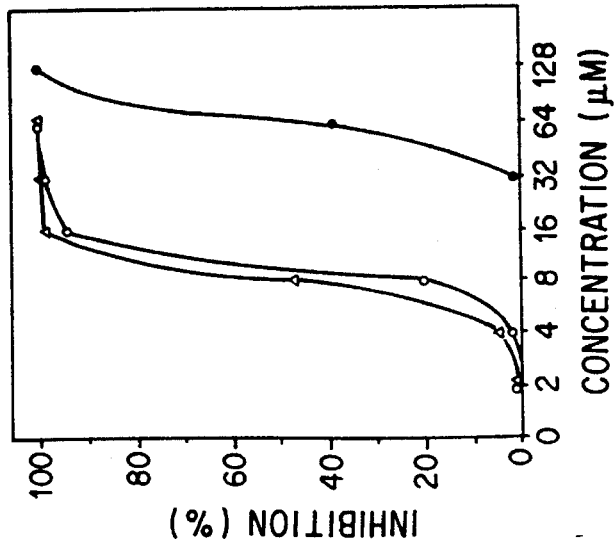

As depicted in FIG. 2, in each case TMS was superior to sphingosine in the ability to inhibit tumor cell growth, (In the figures, the results are presented as the percent of cell growth inhibition relative to control cultures that were not exposed to a test substance.) TMS showed an advantage over DMS although not of the same magnitude. Nevertheless because of the increased efficacy of TMS over DMS, lower amounts were required to effect a specified level of inhibition.

Figure 3:
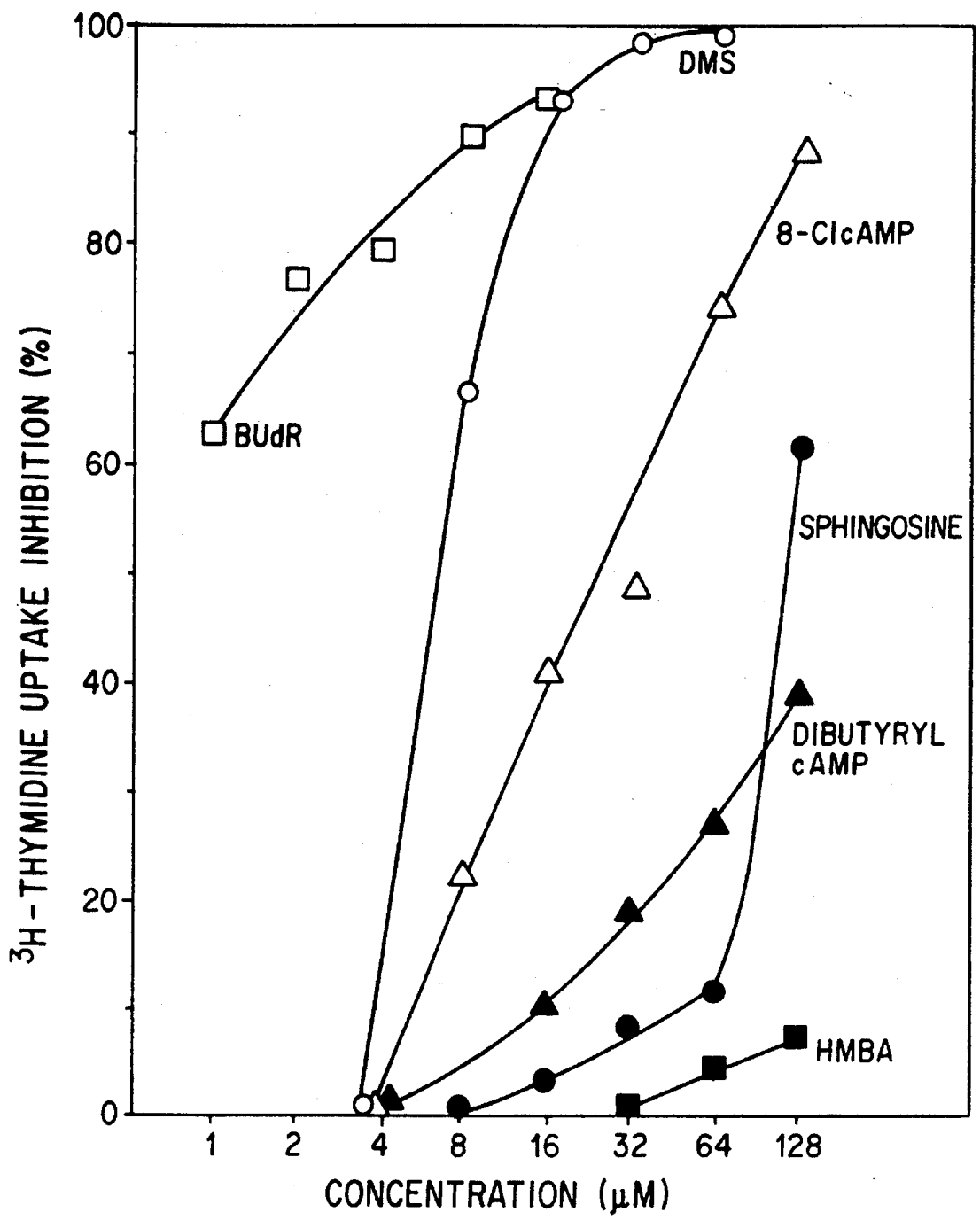
FIG. 3 depicts the comparative effect of various reagents on tumor cell differentiation. MKN-74 cells were exposed to N,N,N-trimethylsphingosine (open squares), N,N-dimethylsphingosine (open circles), 8-chloro-cyclic AMP (open triangles), dibutyryl cyclic AMP (solid triangles), sphingosine (solid circles) and hexamethylenebisacetamide (solid squares).

The enhanced inhibitory activity of TMS is validated in the data summarized in FIG. 3. MKN-74 cells were exposed to cAMP and derivatives thereof and to HMBA, which are known to inhibit tumor cell growth by differentiation induction. Clearly, TMS was the most effective inhibitor of tumor cell growth.

In another in vitro assay, the influence of various compounds on PK-C activity can be monitored. Certain tumor cells present high levels of PK-C activity. The human epidermoid carcinoma cell line A-431 (ATCC No. CRL 1555) can be used in a bioassay for PK-C activity as described in Igarashi et al. (supra). Briefly, phosphatidylserine (5 μg/tube) and 1,2-diolein (0.05 μg/tube), with or without an appropriate quantity of a sphingosine derivative sample, are added in an organic solvent, ethanol or ethanol/chloroform, to a 1.5 ml tube (Sarstedt) and the mixture is evaporated under a N$_2$ stream. The lipid mixture is sonicated in about 30 μl of 20 mM Tris-HCl (pH 7.5) for 30 minutes. The resulting liposomes are supplemented with a buffer mixture comprising 25 mM Tris-HCl (pH 7.5), 10 mM MgCl$_2$, 400 μM EDTA, 50 μM EGTA, 500 μM CaCl$_2$, 200 μg/ml histone III-S or myelin basic protein and 20 μM γ[$^{32}$P]-ATP (2×10$^6$ cpm) to a final volume of about 90 μl.

The reaction is initiated by adding about 10 μl of PK-C, which is prepared from A431 cells as described in Igarashi et al. (supra) or from mouse brain as described in Kikkawa et al. (Biochem. Biophys. Res. Comm., 135, 636, 1986) and containing about 1–2 μg protein, and the mixture is incubated for ten minutes at 30° C. The reaction is terminated by the addition of 1 ml of a 1 mM ATP solution at pH 7.5 containing 25% TCA and 1% BSA. The precipitate is collected by centrifugation, washed twice with 1 ml of 25% TCA, then dissolved in 1 ml of 1M NaOH containing 0.1% deoxycholate with slight heating (80° C. for ten minutes) and counted in a scintillation counter. Reaction mixtures without phosphatidylserine, 1,2-diolein or Ca$^{2+}$ are used as controls.

Data from a series of experiments using two different substrates, histone III-S and myelin basic protein, are summarized in FIG. 4. Regardless of the substrate, TMS was superior to the other compounds in the ability to inhibit PK-C.

Although the data show a superior PK-C inhibitory activity of TMS over the remaining tested compounds, there are other advantages to TMS. Certain cancer cells show a higher metastatic potential and invasive capability than others. For example the BL6 and F10 melanoma cell lines are highly metastatic and invasive. On the other hand, the F1 variant is much less metastatic and invasive (I. R. Hart et al., Amer. J. Pathol., 97, 587–592 (1979); G. Poote et al., Cancer Res. 42, 2770–2778 (1982); F1 and F10 clones from ATCC, CRL 6323 and CRL 6475, respectively).

Figure 5A:
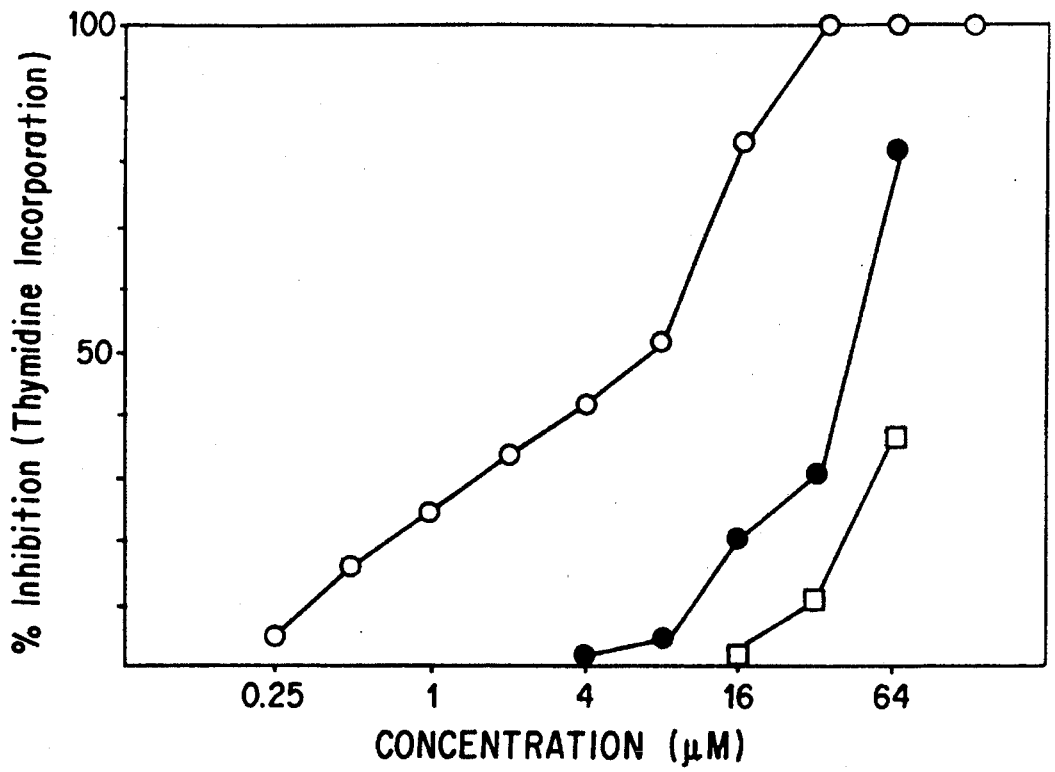
FIGS. 5A and 5B depict the effect of N,N,N-trimethylsphingosine (open circles), N,N-dimethylsphingosine (solid circles) and sphingosine (open squares) on two melanoma cell lines, BL6, a highly malignant cell line (in FIG. 5A) and F1, a cell line of low malignancy, (in FIG. 5B). Cell proliferation was evidenced by tritiated thymidine incorporation into DNA.
Figure 5B:
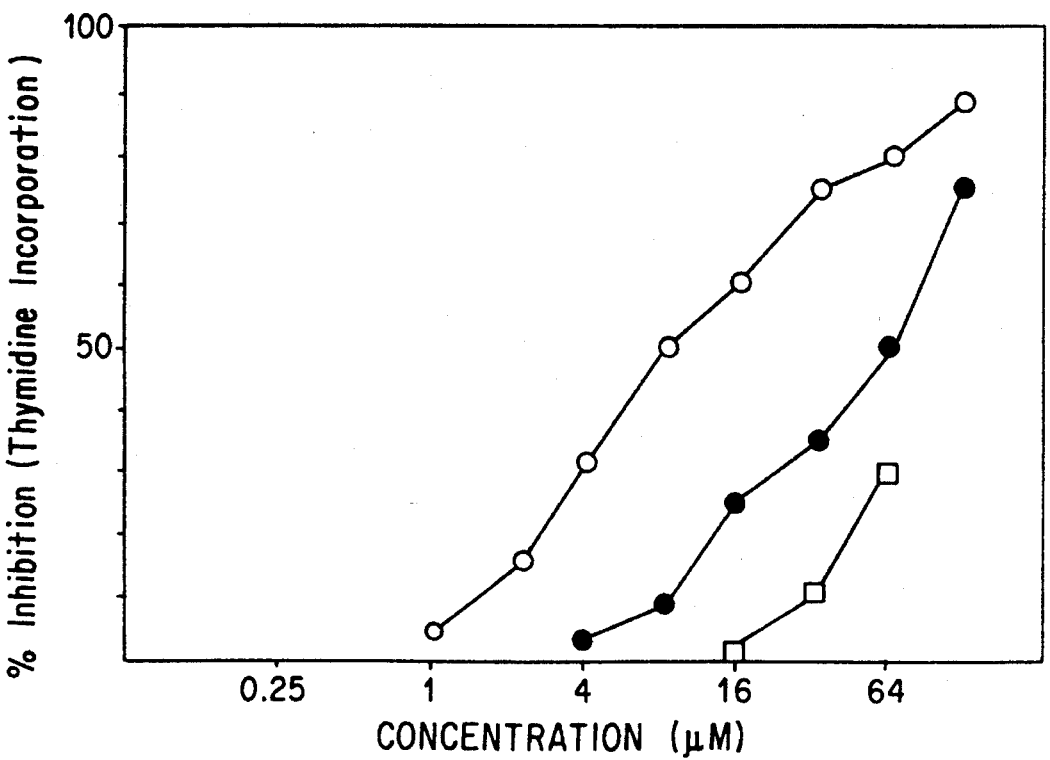

BL6 and F1 cells were tested in vitro as described above. As shown in FIG. 5 TMS was more effective than DMS and sphingosine at inhibiting cell growth. Also BL6 cells were more sensitive to TMS treatment as evidenced by the leftward shift of the TMS curve to lower concentrations.

Figure 6A:
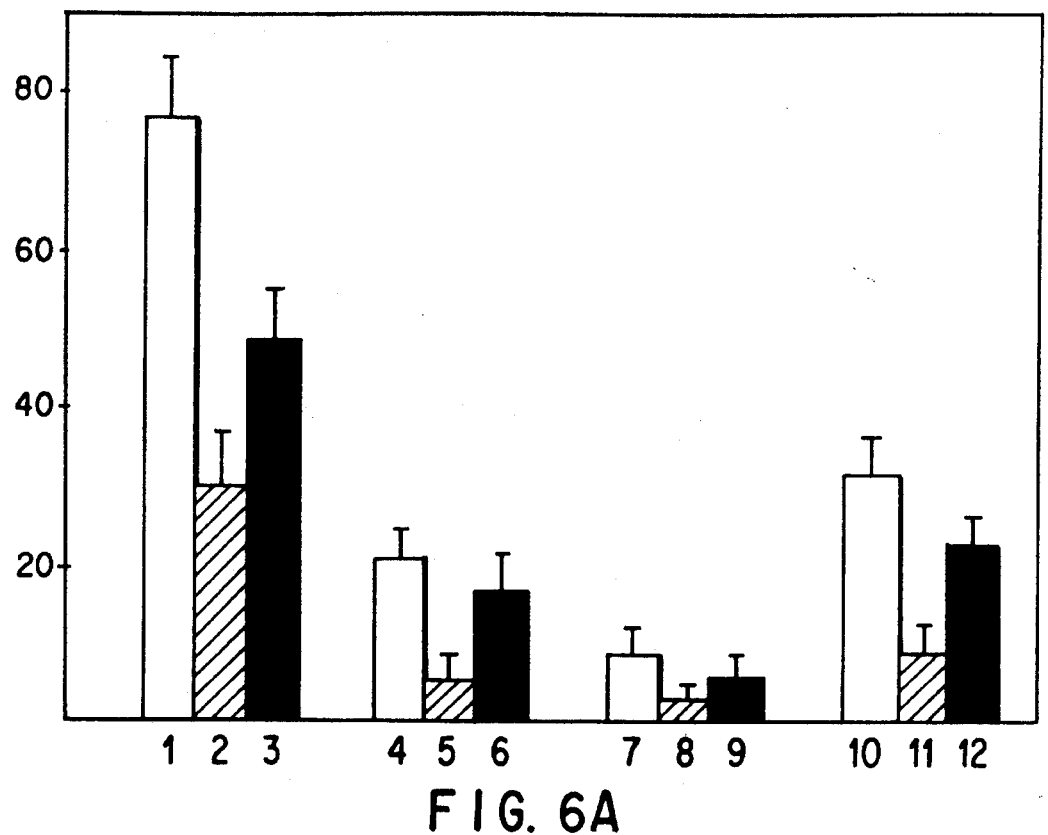
FIGS. 6A–C depict the effect of N,N,N-trimethylsphingosine on lung metastatic deposits after intravenous injection of BL6 cells into mice. Each graph represents the mean and standard deviation of results obtained in 8 animals.
Figure 6B:
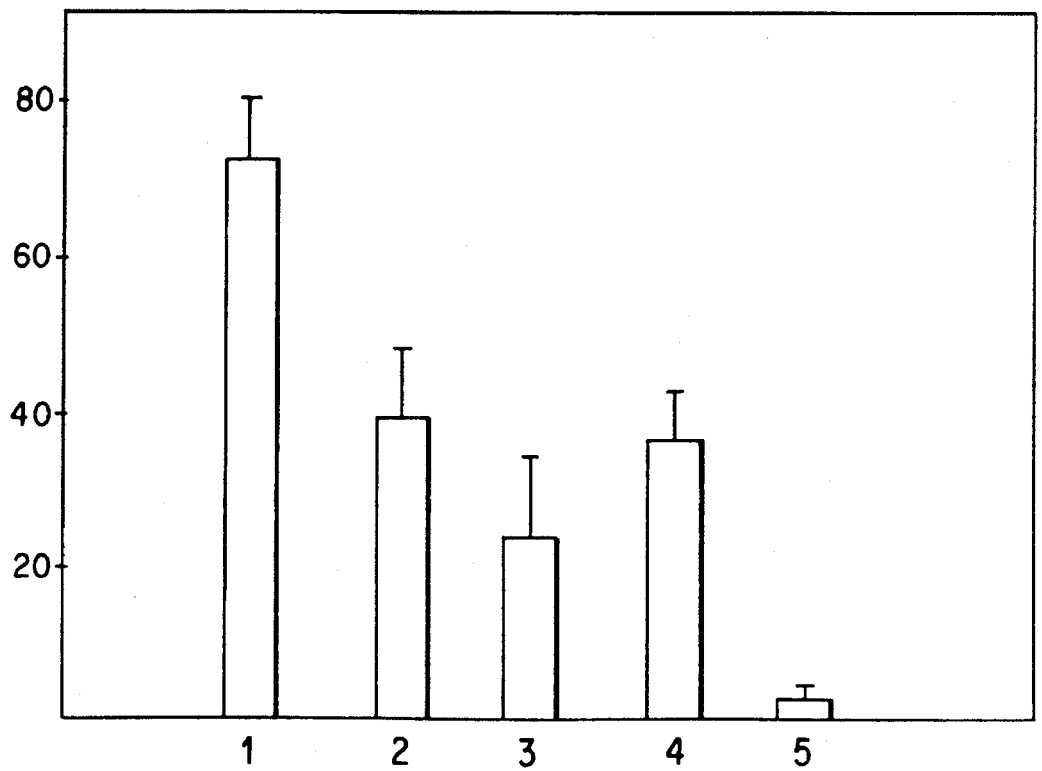
Figure 6C:
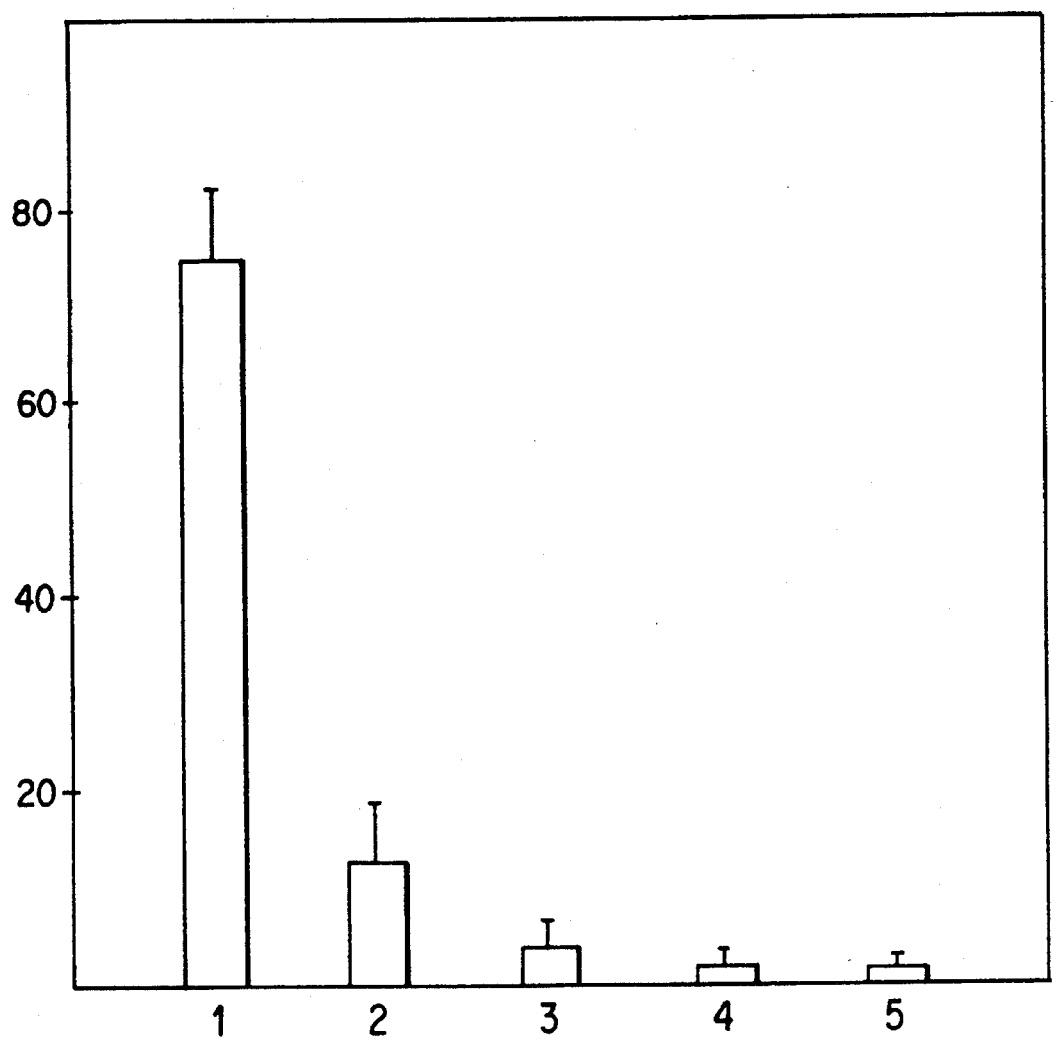

The effectiveness of TMS in vivo is summarized in the graphs comprising FIG. 6. BL6 cells were injected into mice and metastatic deposits in the lung were assessed after various treatments including route and timing of administration. TMS is effective in suppressing lung colonization and tumor development irrespective of route or timing, although early treatment is preferred and repeated treatment is more effective. As revealed in the data summarized in panels B and C, there was a distinct dose responsiveness of lung tumor colonization to TMS.

Figure 7A:
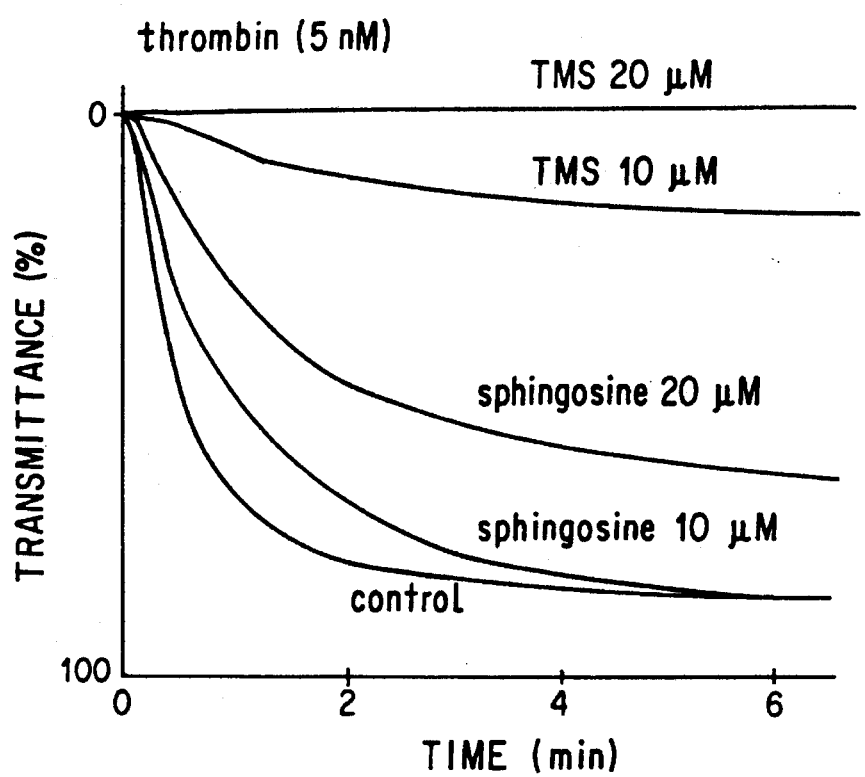
FIGS. 7A and 7B depict the effect of N,N,N-trimethylsphingosine (TMS) on platelet aggregation. A 0.45 ml aliquot of human platelet suspension ($3-5 \times 10^5$ platelets per µl of Tyrode's buffer) was incubated with sphingosine or TMS for 2 minutes. Then platelet aggregation was induced by the addition of either γ-thrombin (FIG. 7A) or adenosine diphosphate (ADP) (FIG. 7B) in 0.05 ml. The degree of aggregation was determined in an aggregometer and the data analyzed with an integrated computer (Kyoto Daiichi Kagaku Co. Ltd.).
Figure 7B:
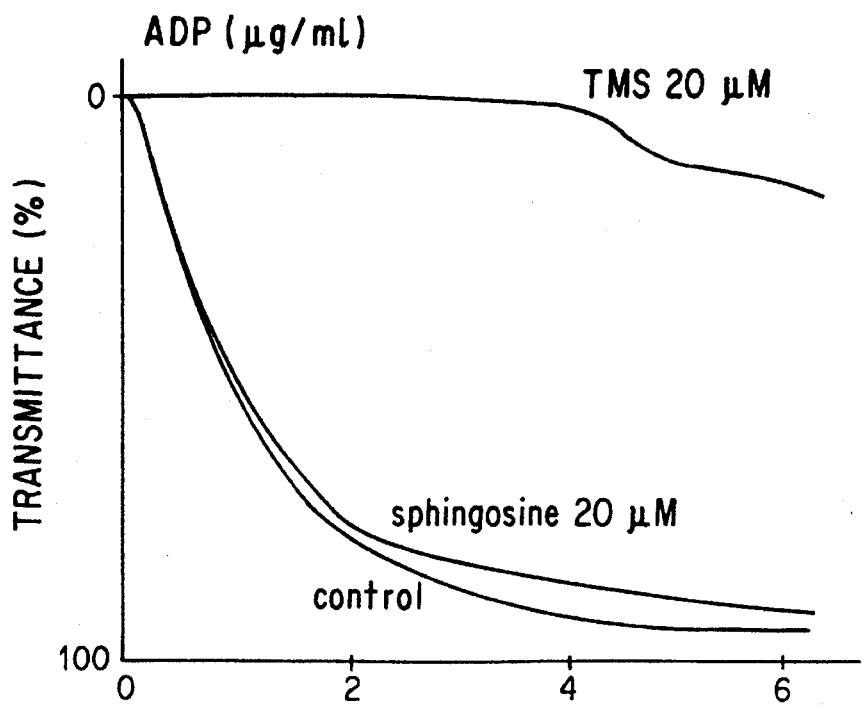
Figure 8:
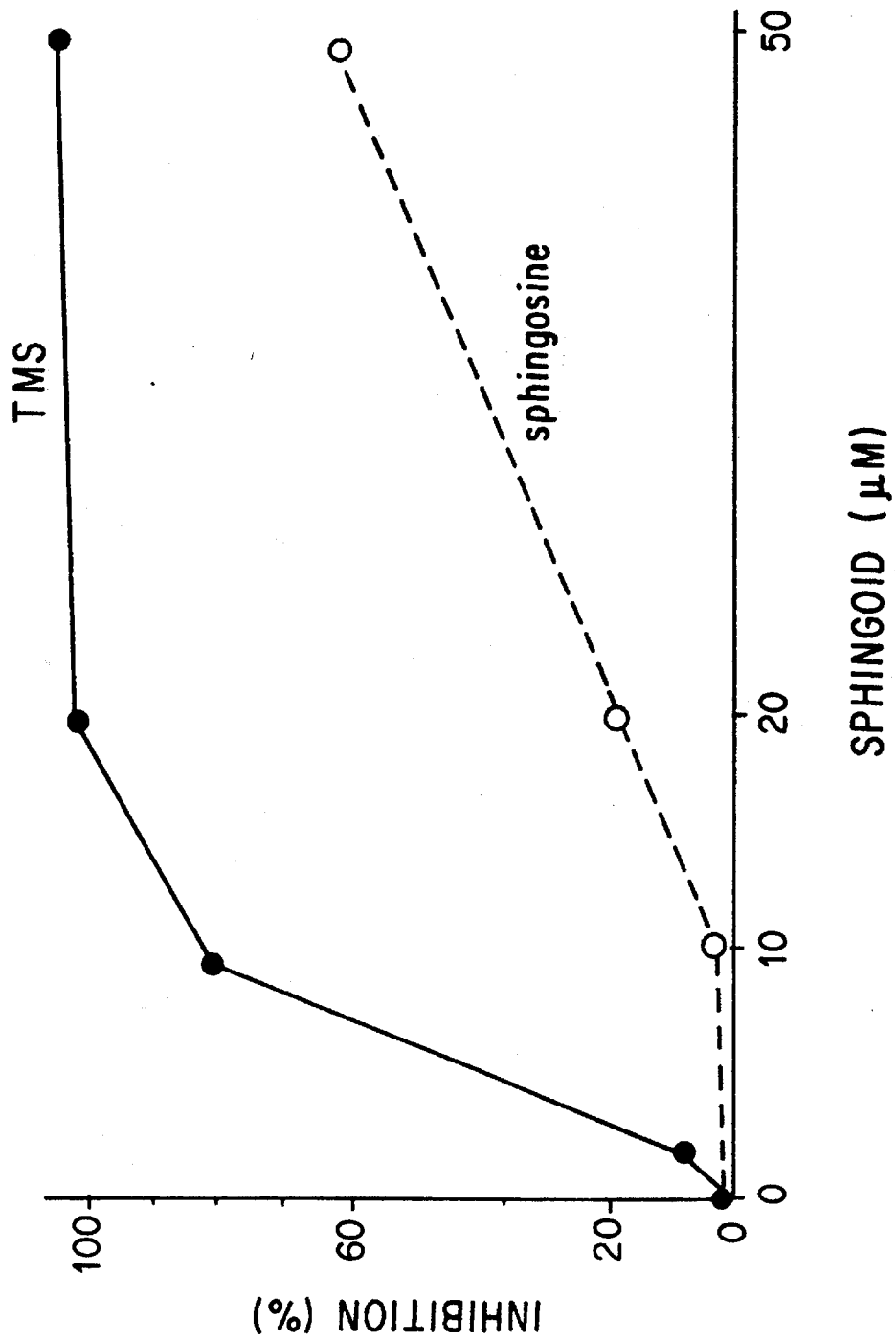
FIG. 8 depicts further the dose response of platelet aggregation by sphingoid. Aggregation of the platelets was induced with 10 nM γ-thrombin.

Another aspect of TMS is the profound effect it has on platelet aggregation (for the purposes of the instant invention, platelets are considered cells). As presented in the data summarized in FIGS. 7 and 8, TMS inhibited platelet aggregation in a dose-responsive fashion.

Figure 9:
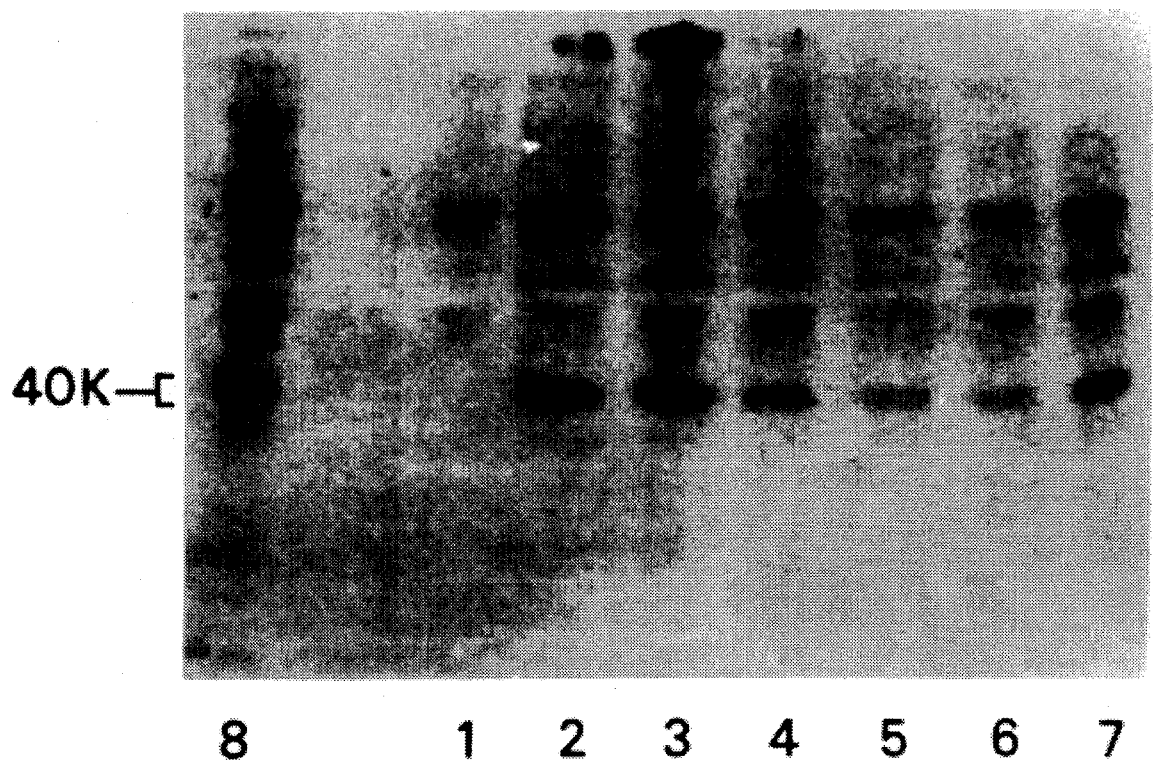
FIG. 9 depicts the inhibition of γ-thrombin-induced phosphorylation of 40 kD protein of human platelets by sphingosine and TMS. Human platelets ($3 \times 10^5$/µl) were prelabeled with $^{32}$p-phosphoric acid (0.2 mCi/ml) in Tyrode's buffer containing 22 mM trisodium citrate, 1 mg/ml glucose and 3.5 mg/ml bovine serum albumin (pH 6.5) for 75 minutes at 37° C. After centrifugation (600× g, 10 minutes), the platelets were resuspended in Tyrode's buffer (pH 7.2), aliquoted in plastic tubes and pre-incubated at 37° C. for 5 minutes with various concentrations of sphingosine and its derivatives (added as 50% ethanol solutions with a final ethanol concentration of 0.5%). Platelets then were stimulated with thrombin (10 µM). The reactions were stopped after 30 seconds by the addition of 5× sample buffer, the samples were boiled and loaded onto 10% SDS-polyacrylamide gels. The proteins were separated electrophotectically. Lane 1-control without stimulation by thrombin; Lane 2-stimulation by 1 µU/ml of γ-thrombin; Lane 3-stimulated by thrombin but added with 1 µM TMS; Lane 4-stimulated by thrombin but added with 10 µM TMS; Lane 5-stimulated by thrombin but added with 20 µM TMS; Lane 6-stimulated by thrombin but added with 30 µM TMS; Lane 7-stimulated by thrombin but added with 20 µM sphingosine; Lane 8-stimulated by thrombin but included addition of 20 µM N,N-dimethylsphingosine.

Upon thrombin stimulation, a 40 kD platelet protein is phosphorylated. As noted in FIG. 9, TMS exposure inhibits phosphorylation of the 40 kD platelet protein. While not wanting to be bound by their statement, the inventors believe that absence of phosphorylated 40 kD protein prevents platelet aggregation.

Platelet activation is of central importance for initiation of numerous biological processes related to hemostasis, inflammation, wound healing and tumor cell metastasis and invasion. There are many factors and mechanisms which influence platelet activation and many consequences of activation. The selectin GMP-140 binds to neutrophils, HL60 cells or tumor cells which express sialosyl-Le$^x$. Mechanisms of expression of GMP-140 and its subsequent binding to sialosyl-Le$^x$ are of central importance for initiation of inflammatory processes as well as tumor cell metastasis. GMP-140 expression is down-regulated or blocked by preincubation with TMS. The possibility of a cytotoxic effect of TMS on platelets is excluded clearly by the fact that platelets show normal ristocetin-induced aggregation following incubation with TMS.

The utility of TMS is not limited to the suppression of malignant cell growth. Inflammation is characterized in part by a proliferation of lymphoid and myeloid cells. Generally the proliferation serves a beneficial purpose, such as sequestration of foreign antigen or enhancement of restorative capabilities following an insult, but at times can occur abnormally, for example as a result of an autoimmune dysfunction. Thus TMS has utility in controlling cell proliferation of apparently normal cells.

For example, mouse CTLL-2 cells (ATCC No. TIB 214), a T lymphocyte cell line, were plated at $1.5 \times 10^4$ cells per well and exposed to test substances. Cell proliferation was monitored by thymidine incorporation. The data of several experiments are summarized in FIG. 10. TMS was effective in suppressing CTLL-2 cell growth.

Accordingly, the present invention provides a method for inhibiting growth of human and animal cells comprising the step of exposing said human or animal cells to a cell growth inhibiting amount of N,N,N-trimethylsphingosine or pharmaceutically acceptable salts thereof.

Because TMS has an inhibitory activity on protein kinase C and other kinases, TMS likely prevents the expenditure of intracellular ATP stores and hence dampens metabolic activity, in addition to the platelet aggregating inhibiting and cell adhesion inhibiting activities described herein. Thus, TMS can be used to preserve or to prolong storage of biologic materials, such as blood products.

For example, it has been shown that TMS retards erythrocyte metabolic activity in vitro under normal blood storage conditions as evidenced by a reduction of erythrocyte enzyme activity. Similar results can be expected for leukocytes and platelets.

Accordingly, TMS can be used as an adjunct to methods and formulations now in use for the preservation or storage of biologic materials. A cell growth inhibiting amount of TMS can be added to the storage medium.

Neutrophils (polymorphonuclear leukocytes) display three major agonist-dependent responses which normally are manifest in three major functions: (i) an exidative burst to produce superoxide ($O_2$-); (ii) phagokinetic migratory activity; and (iii) the ability to interact with activated endothelial cells (EC's) and platelets. Mechanisms (ii) and (iii) result in adhesion to EC's and migration through the EC monolayer into the vascular or extravascular matrices. Normally, the functions collectively provide a useful mechanism for disposing of microorganisms in an inflammatory type response. However, accumulation and overfunction of neutrophils during inflammatory disorders can result in tissue damage and circulatory disturbances.

Neutrophil responses are triggered by numerous stimuli, including chemotactic peptides (e.g., formyl-met-leu-phe (fMLP), arachidonate, short-chain diacylglycerol (DAG, C8-DAG) and phorbol esters (e.g., PMA).

Figure 13A:
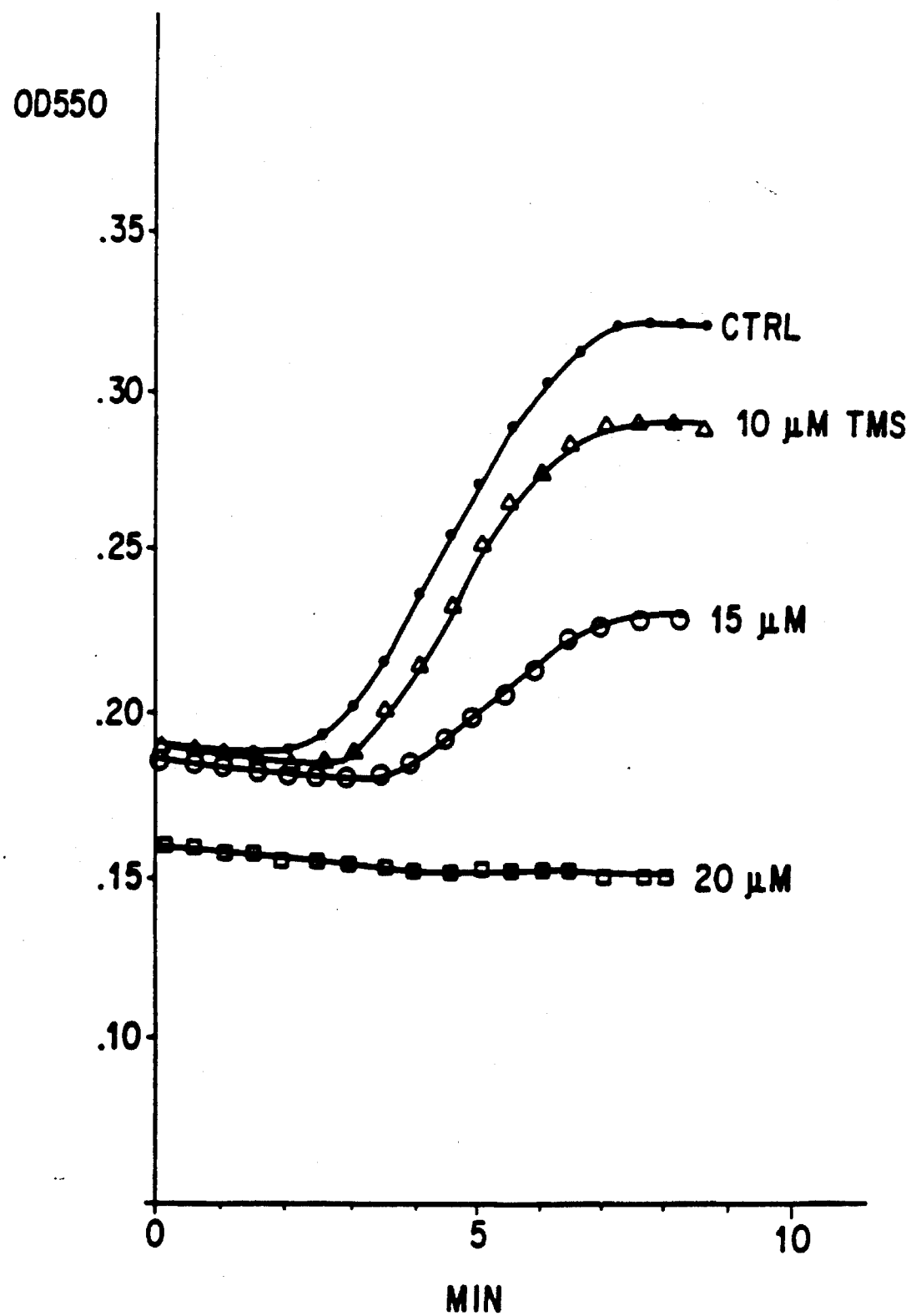
FIGS. 13A and 13B depict the effect of various reagents on neutrophil function.
Figure 13B:
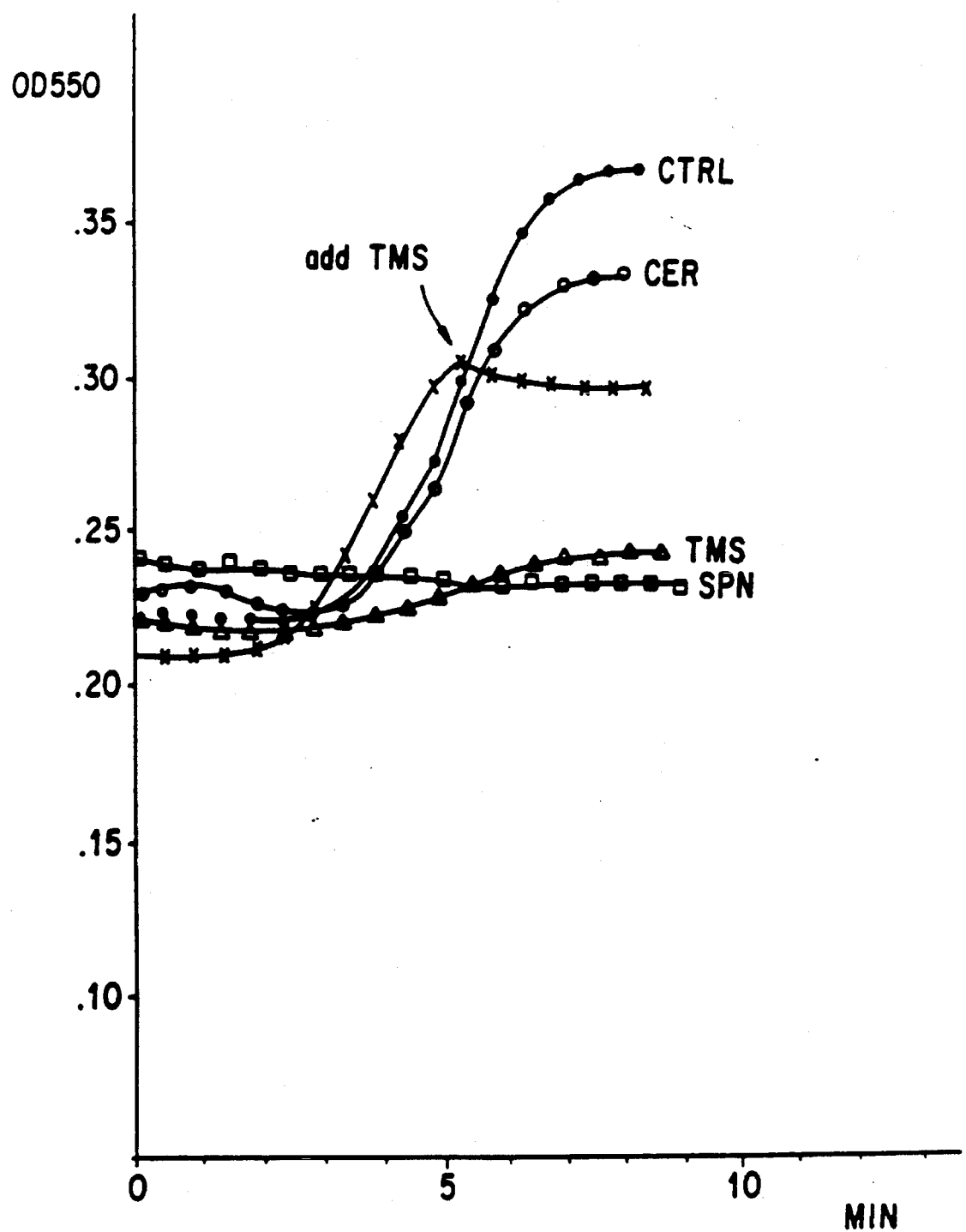
Figure 14:
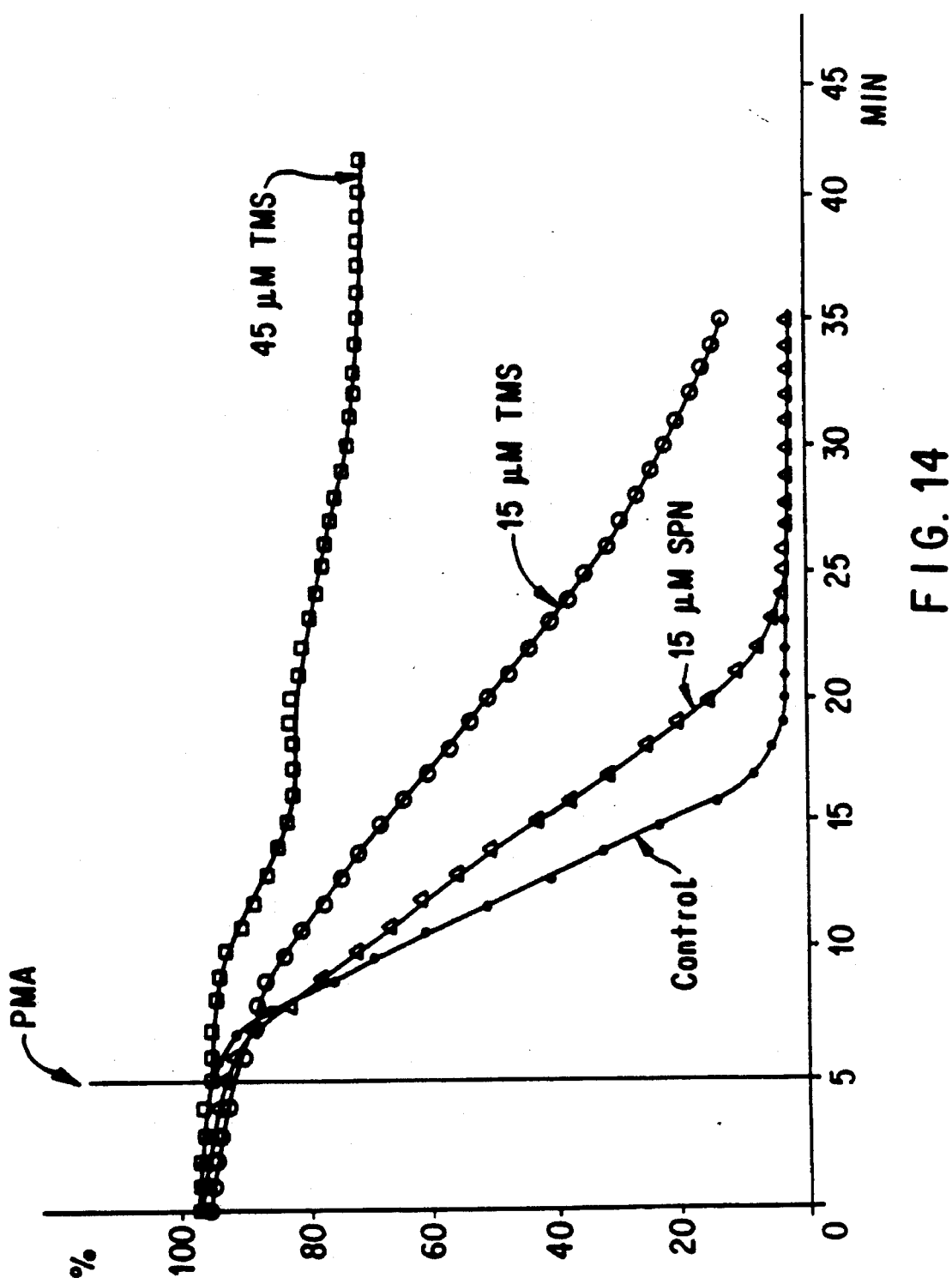
FIG. 14 depicts the effect of various reagents on neutrophil $O_2$ consumption. The Clark-type electrode and oxygen monitor were calibrated using air-saturated water according to the manufacturer's recommendations (Y.S.I. Inc., Yellow Springs, Ohio. A reading of 100% was considered to be equal to the concentration of oxygen in air-saturated water.

Superoxide production in neutrophils obtained using art-recognized methods, for example, see Nojiri et al., Blood, 64, 534, 1984, as determined by reduction of cytochrome C, is inhibited by TMS in a dose-dependent manner (FIGS. 13A and 13B). TMS (20 μM) completely abolishes superoxide production. (The reduction of cytochrome C is monitored using known methods, such as the method of Clifford, Meth. Enz., 105, 393, 1981. $O_2$ consumption of neutrophils, as determined by electrical conductivity using an oxygen monitor and micro $O_2$ chamber assembly (Y.S.I. Inc., Yellow Springs, Ohio), is enhanced significantly by PMA. The PMA-dependent enhancement of $O_2$ consumption is inhibited strongly by TMS (FIG. 14).

The phagokinetic activity of neutrophils on gold sol-coated plates can be determined by a technique essentially as taught in Albrecht-Buehler (Cell, 11, 395, 1977). Phagokinetic activity is suppressed significantly by as little as 1.5 μM TMS and completely suppressed by 4.5 μM TMS. The TMS-dependent inhibitory effect is reversed completely when the culture medium is replaced with TMS-free medium. Thus, the inhibitory effect of TMS on phagokinetic activity is not dependent on cytotoxicity.

A characteristic of neutrophils is the ability to adhere to activated EC's and to migrate through the EC monolayer into the vascular or extravascular matrix. The effect of TMS on neutrophil interactions with EC's and their subsequent trans-endothelial migration thereof can be monitored in vitro using human umbilical endothelial cells (HUVEC's) (Luscinskas et al., J. Imm., 146, 1617, 1991). Neutrophils are added to a HUVEC monolayer and neutrophil-HUVEC interactions are assessed microscopically following fixation, embedding and staining of monolayer sections.

Under physiological conditions, neutrophils are able to migrate into the collagenous matrix through the EC monolayer. When EC's are activated with IL-1β in M199 medium for 4 hours, neutrophils migrate into the collagenous matrix within 90 minutes. Neutrophil migration is inhibited strongly by pre-treatment of neutrophils with 8 μM TMS, and completely inhibited by pre-treatment with 25 μM TMS.

The dose-dependent inhibitory effect of TMS and other protein kinase inhibitors on migration of neutrophils through the IL-1β-activiated EC monolayer is summarized in Tables I and II. TMS (15 μM) greatly reduces the number of cells migrating through the EC monolayer without affecting the viability of the cells. Calphostin C (5 μM), 200 μM H7 and 2 μM staurosporine produce similar cytotoxic effects on neutrophils although staurosporine and calphostin C produce striking morphologic damage to EC's (Tables III and IV).

TMS (15 μM) shows no significant cell cytotoxicity whereas 15 μM SPN and 15 μM DMS show 12–13% cytotoxicity. At 25 μM, SPN and DMS produce

TABLE I

Suppression of phagokinetic activities by protein kinase inhibitors

| Inhibitor† | Area Swept | N |
|---|---|---|
| CONTROL | 100 ± 25%* | 178 |
| TMS (4.5 μM) | 16 ± 18 | 93 |
| SPN (4.5 μM) | 14 ± 7 | 72 |
| DMS (4.5 μM) | 26 ± 25 | 132 |
| H-7 (200 μM) | 27 ± 6 | 75 |
| Staurosporine (0.2 μM) | 13 ± 12 | 68 |
| Calphostin C (0.5 μM) | 39 ± 11 | 65 |
| Ceramide (4.5 μM) | 109 ± 25 | 62 |

*mean ± sample standard deviation
§ The area swept by neutrophils was determined in photographs of the monolayers. The regions cleared by neutrophil movement were then cut out and weighted.
† H-7 was obtained from Seikagaku Kogyo (Tokyo, Japan); staurosporine and calphostin C were obtained from Kamiya Biochemical Co. (Thousand Oaks, CA); and ceramide was obtained from Sigma.

TABLE II

Effect of TMS and ceramide on neutrophil transmigration

| μM | TMS | Ceramide |
|---|---|---|
| 0 | 100 ± 17* | 100 ± 17 |
| 4 | 96 ± 18 | 92 ± 24 |
| 8 | 66 ± 28 | ND |
| 15 | 41 ± 8.7 | 87 ± 27 |
| 25 | 6.8 ± 4.1 | ND |
| 45 | 1.2 ± 1.2 | 83 ± 16 |

*mean ± sample standard deviation (N = 25)
Cross-sections (2 μm) of the collagen bed with HUVEC's and neutrophils were observed using a Zeiss light microscope with KPL W10 ahd Ph2 Neofluar 16 lenses. The number of cells transmigrated were counted for each view.
ND = Not Done.

TABLE III

Effect of various PKC inhibitors on neutrophil transmigration through endothelial monolayers

| Effectors | Number of Cells/View | Viability |
|---|---|---|
| control | 100 ± 14* | 94 ± 2.1 |
| 15 μM TMS | 39 ± 17 | 97 ± 2.9 |
| 15 μM SPN | 36 ± 12 | 87 ± 5.3 |
| 200 μM H-7 | 38 ± 12 | 79 ± 7.1 |
| 2 μM Staurosporine | 52 ± 25 | 83 ± 3.6** |

TABLE III-continued

Effect of various PKC inhibitors on neutrophil transmigration through endothelial monolayers

| Effectors | Number of Cells/View | Viability |
|---|---|---|
| 5 μM Calphostin C | 19 ± 8.9 | 46 ± 5.5** |

*mean ± sample standard deviation (N = 25)
**significant morphologic damage to HUVEC's.

TABLE IV

Recovery of phagokinetic activity from effectors*

| Treatment | Area Swept | N |
|---|---|---|
| control (w/o further incubation) | 100 ± 25† | 178 |
| control (0.1% ethanol) | 92 ± 30 | 118 |
| TMS (12 μM) | 92 ± 34 | 77 |
| SPN (12 μM) | 42 ± 24 | 86 |
| DMS (12 μM) | 32 ± 19 | 112 |

†mean ± sample standard deviation
*Neutrophils were pre-incubated with 12 μM of the noted treatment for 10 minutes in test tubes and then distributed to the monolayers. The treatment reagents were diluted 200-fold following that procedure.

TABLE V

Viability of neutrophils

| μM | Ceramide | TMS | SPN | DMS |
|---|---|---|---|---|
| 0 | 97 ± 3* | 97 ± 3 | 97 ± 3 | 97 ± 3 |
| 5 | 98 ± 2 | 98 ± 2 | 95 ± 3 | 96 ± 3 |
| 15 | 96 ± 1 | 97 ± 3 | 87 ± 5 | 88 ± 8 |
| 25 | — | 83 ± 6 | 53 ± 18 | 29 ± 5 |
| 45 | 91 ± 3 | 63 ± 8 | 5 ± 5 | 0 ± 1 |

*mean ± sample standard deviation (N = 8)
The concentration of neutrophils ranged from 0.8 to 1.7 × 10⁶/ml. The viability was evaluated by trypan blue exclusion assay. The cell suspension in RPMI 1640 with glutamate and pyruvate without FCS was incubated at 37° C. for 10 min with effectors. The aliquot was mixed with an equal amount of trypan blue solution and immediately counted under a Nikon light microscope.

major cytotoxic damage to neutrophils whereas the effect of TMS is negligible (Table V).

When neutrophils, metabolically labeled with [$^{32}$P]sodium phosphate (2 mCi) for 1 hr to enrich intracellular ATP, are stimulated with 1.5 μM PMA, two protein bands following SDS-PAGE show greatly enhanced phosphorylation. The proteins have molecular weights of about 47 kDa and 65 kDa. When neutrophils are pre-incubated with 15–45 μM SPN, DMS or TMS and then stimulated with PMA, phosphorylation of both proteins is diminished significantly. The inhibitory effect on phosphorylation is observed within 2 minutes of incubation. Because phosphorylated 47 kDa and 65 kDa proteins appear to be direct substrates of PK-C, the inhibitory effects of SPN, DMS, and TMS may occur via an inhibitory effect on PK-C.

Metabolic incorporation of [$^{32}$P]sodium phosphate (4 mCi) into phosphatidylinositol (PI), phosphatidylinositol-4-phosphate (PIP) and phosphatidylinositol-4,5-bis-diphosphate (PIP2) is enhanced by chemotactic peptide fMLP (1 μM). The fMLP-dependent enhancement is suppressed strongly by pre-incubation of neutrophils with 5 μM TMS. Relative intensity of fMLP-induced labeling in PIP and PIP2, and the effects of SPN, DMS and TMS on metabolic incorporation of $^{32}$P into PIP and PIP2 are summarized in Table VI.

TABLE VI

Effect of TMS, DMS and SPN on phosphoinositide turnover

| Effector | PIP | PIP2 |
| --- | --- | --- |
| control | 100 | 100 |
| 1 µM fMLP | 182 ± 39* | 147 ± 32 |
| 5 µM TMS plus fMLP | 127 ± 19*[2] | 98 ± 7.2*[3] |
| 5 µM SPN plus fMLP | 174 ± 37 | 128 ± 13 |
| 5 µM DMS plus fMLP | 146 ± 27 | 109 ± 17*[1] |

*, mean ± sample standard deviation (N = 6)
*1, $p < 0.05$
*2, $p < 0.02$
*3, $p < 0.01$ Amount of $^{32}P$ in PIP and PIP2 was measured using TLC separation. The spots on TLC plates were scraped off and the radioactivity therein was measured with a Beckman scintillation counter. Each spot was compared as to intensity with the identical spot of the control sample.

The present invention further provides medicaments and treatments for inhibiting growth in human and animal cells and aggregation of human and animal platelets comprising:

(1) a therapeutically effective amount of N,N,N-trimethylsphingosine or pharmaceutically acceptable salts thereof; and (2) a pharmaceutically acceptable carrier, diluent or excipient.

The medicaments and methods are applicable both for in vitro and in vivo applications. Specific uses include treatment of malignancies, benign tumorous growths, inflammation, other manifestations of immune system dysfunction and when the immune system inappropriately or excessively responds to a stimulus.

The medicament comprises an effective amount of TMS and a pharmaceutically acceptable carrier, diluent or excipient. The effective amount of TMS can be determined using art-recognized methods, such as by establishing dose-response curves in suitable animal models, such as described herein or in non-human primates, and extrapolating to human; extrapolating from suitable in vitro data, for example as described herein; or by determining effectiveness in clinical trials.

Trimethylsphingosine also has profound effects on cell adhesion molecules. The effect is evidenced by the inhibition of cell adhesion molecule expression by platelets. For example thrombin induces expression of GMP-140 in platelets. However, exposure of platelets to TMS inhibits GMP-140 expression. Thus, TMS will be useful in disorders that rely on cell adhesion molecule dependent-processes. As noted above, GMP-140, as does ELAM-1, binds sialosyl-Le$^x$. Thus TMS will find utility in preventing lymphocyte-endothelial cell adhesion and subsequent interactions between cells such as the development of an inflammatory state at a site of injury.

Suitable doses of medicaments of the instant invention depend upon the particular medical application, such as the severity of the disease, the weight of the individual, age of the individual, half-life in circulation etc., and can be determined readily by the skilled artisan. The number of doses, daily dosage and course of treatment may vary from individual to individual.

TMS can be administered in a variety of ways such as orally, parenterally and topically. Suitable pharmaceutically acceptable carriers, diluents, or excipients for the medicaments of the instant invention depend upon the particular medical use of the medicament and can be determined readily by the skilled artisan.

The medicament can take a variety of forms such as tablets, capsules, bulk or unit dose powders or granules; may be contained within liposomes; or may be formulated into solutions, emulsions, suspensions, ointments, pastes, creams, gels, foams or jellies. Parenteral dosage forms include solutions, suspensions and the like. The medicament is likely to contain any of a variety of art-recognized excipients, diluents, fillers etc. Such subsidiary ingredients include disintegrants, binders, lubricants, surfactants, emulsifiers, buffers, moisturizers, solubilizers and preservatives. The artisan can configure the appropriate formulation comprising TMS and seeking guidance from numerous authorities and references such as "Goodman & Gilman's, The Pharmaceutical Basis of Therapeutics" (6th ed., Goodman et al., eds., MacMillan Publ. Co., N.Y., 1980).

In body sites that are characterized by continual cell growth or require cell growth inhibition because of dysfunction and are relatively inaccessible, TMS can be administered in a suitable fashion to assure effective local concentrations. For example, TMS may be injected in a depot or adjuvant, carried in a surgically situated implant or reservoir that slowly releases a fixed amount of TMS over a period of time or may be complexed to recognition molecules with the capability of binding to the site presenting with abnormal cell growth. An example of such a contemplated scenario is a recognition molecule that is an antibody with binding specificity for a bone marrow specific antigen wherein said marrow specific antibody is complexed to TMS, said complex administered to a patient with leukemia.

Certain aspects of the invention are described in the following non-limiting Examples. Unless otherwise indicated, all amounts and measures are in w/v or v/v relationships.

EXAMPLE 1

Platelets were isolated from platelet-rich plasma (purchased from the Oregon Red Cross, Portland, Oreg. Contaminating erythrocytes were removed by centrifugation (80×g for 10 minutes). Platelets were obtained by centrifugation (300×g for 10 minutes), washed once in Tyrodes's buffer (pH 6.5) containing 22 mM trisodium citrate and 0.35% (w/v) BSA and resuspended in the same buffer to obtain a concentration of 1–2×10$^9$ platelets/ml. All procedures were performed at room temperature.

A suspension of platelets (3.5×10$^8$/ml) in Tyrode's buffer was preincubated with various inhibitor compounds (H-7 is [1-(5-isoquinolinylsulfonyl)-2-methylpiperazine, a synthetic protein kinase-C inhibitor purchased from Seikagaku America Inc., St. Petersburg, Fla.], calphostin-C [a synthetic protein kinase-C inhibitor obtained from Dr. Saitoh, Kyowa Hakko Co., Ltd., Machida, Tokyo, Japan], sphingosine [purchased from Sigma, St. Louis, Mo.] and dimethylsphingosine and trimethylsphingosine [synthesized according to Igarashi et al., Biochem., 28, 6796, 1989]) followed by addition of thrombin or ADP (both purchased from Sigma). Platelet aggregation was evaluated by transmittance change using an aggregometer (Chrono-log Corp., Havertown, Pa.) equipped with a computer analyzer.

TMS inhibited platelet aggregation.

EXAMPLE 2

GMP-140 expression was determined by (i) flow cytometry with mAb AC1.2, which is directed to GMP-140 and obtained from Dr. Furie (Tufts Univ. Sch. Med., Boston, Mass.) and (ii) adhesion of HL60 cells on platelet-coated solid phase.

A suspension of platelets (1×10⁸/ml) in Tyrode's buffer was preincubated with inhibitor at pH 7.2, 37° C., for 5 minutes, then supplemented with activator, either thrombin (final concentration 1 U/ml) or phorbol 12-myristate 13-acetate (PMA (final concentration $10^{-7}$M), and the mixture was incubated at 37° C. for 10 minutes. Platelets were fixed with an equal volume of 2% (w/v) paraformaldehyde in PBS and washed 2 times with PBS containing 1% (w/v) BSA.

The paraformaldehyde-fixed platelets were incubated with 50 µl of mAb AC1.2 (2.5 µg/ml) at room temperature for 30 minutes. Platelets were washed 2 times with PBS containing 1% (w/v) BSA, supplemented with 50 µl of fluorescein isothiocyanate-labeled goat anti-mouse Ig (purchased from Tago Co., Burlingame, Calif.), incubated at room temperature for 30 minutes and again washed 2 times with PBS containing 1% (w/v) BSA. As a negative control, paraformaldehyde-fixed platelets were incubated with mouse IgG instead of mAb AC1.2 and treated as described above.

The platelets were analyzed in an Epics flow cytometer (Coulter Corp.) with suitable gating. To calculate the inhibitory effect of various reagents, the mean fluorescence intensity of resting platelets (obtained on incubation of platelets without activator) was subtracted from the value for the activated platelet sample.

Figure 11B:
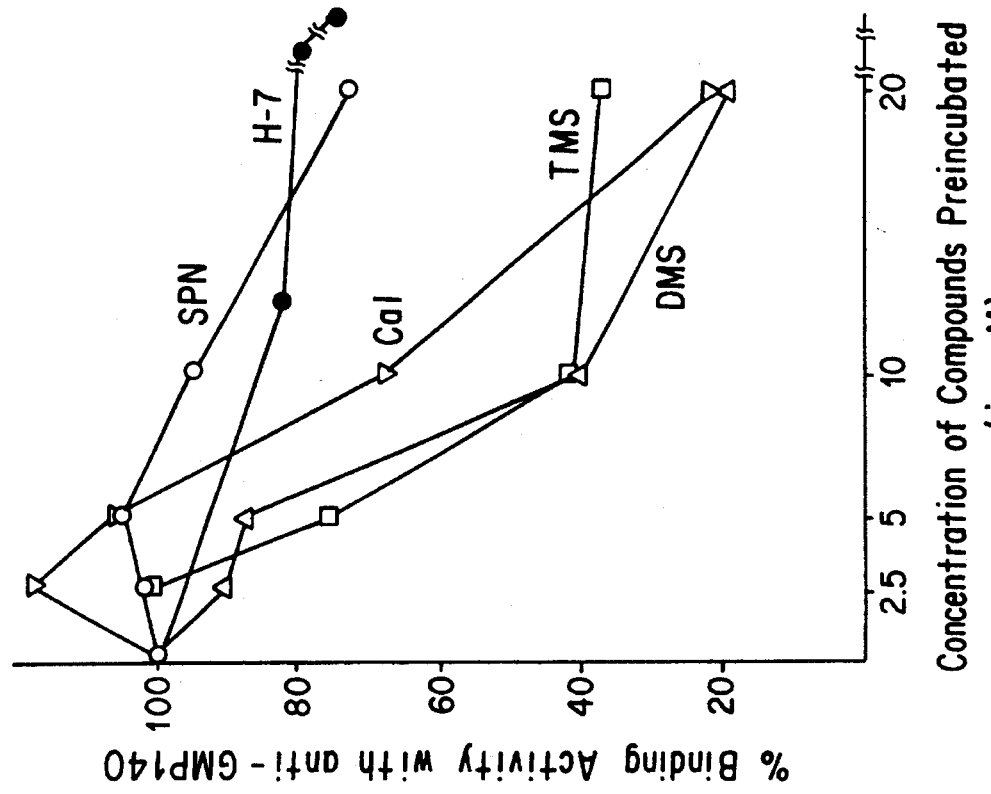
FIGS. 11A and 11B depict results of representative experiments assessing the percentage of platelets capable of binding an anti-GMP-140 antibody following exposure to various agents. The percentage binding activity was determined in a flow cytometer. SPN is sphingosine; H-7 is 1-(5-isoquinolinylsulfonyl)-2-methylpiperazine; Cal is calphostin-C; TMS is trimethylsphingosine; and DMS is dimethylsphingosine.
Figure 11A:
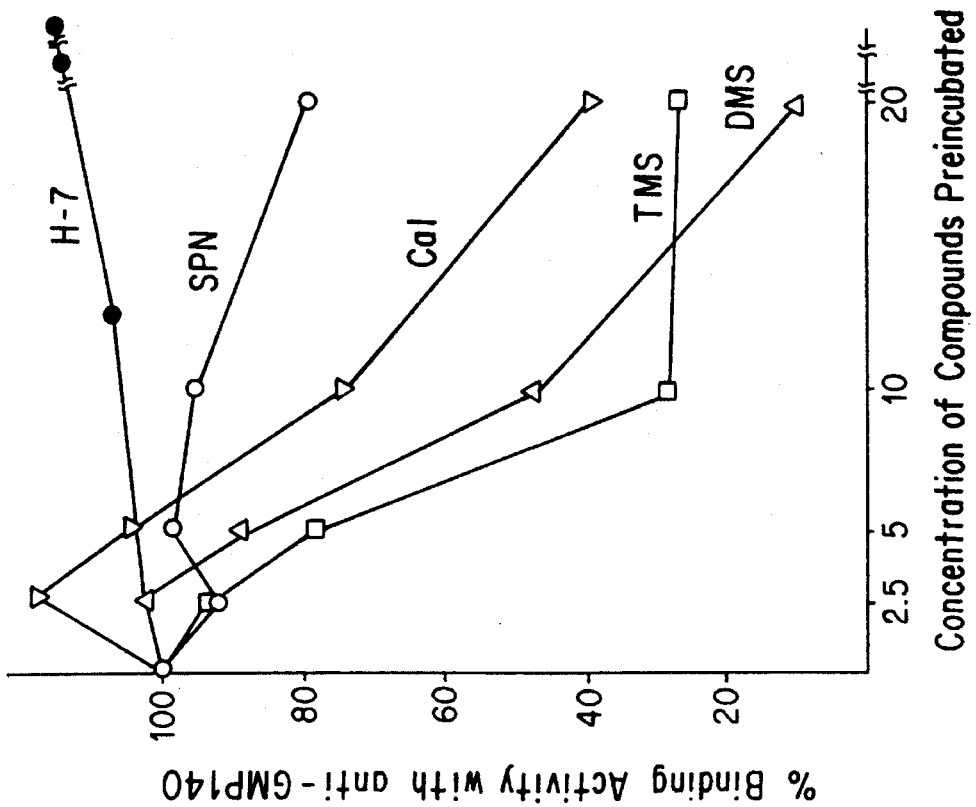

Results of representative experiments are summarized in FIGS. 11A and 11B. TMS at 10–20 µM strongly inhibited GMP-140 expression. While DMS did not inhibit thrombin- or ADP-induced platelet aggregation as well as did TMS, DMS strongly inhibited thrombin-induced GMP-140 expression. SPN and H-7 produced no inhibition of GMP-140 expression. Calphostin-C produced weak inhibition at 10–20 µM [The compound has been reported to inhibit protein kinase-C at a concentration of 0.05 µM in vitro (Tamaoki & Nakano, Bio/Tech., 8, 732, 1990).].

Similar results were obtained for PMA-induced platelets, i.e., both TMS and DMS, at 10–20 µM, strongly inhibited GMP-140 expression (FIG. 11B). Neither SPN nor H-7 showed inhibition, even though H-7 was reported to inhibit PKC at a concentration of 15 µM (Tamaoki & Nakano, supra).

EXAMPLE 3

HL60 (a human promyelocytic cell line available from the ATCC under accession number CCL 240) adhesion on resting or activated platelet-coated solid phase was evaluated as follows. Each well of a 48-well plate (Costar Scientific, Cambridge, Mass.) was filled with a poly-L-lysine solution (100 µg/ml in PBS) and incubated for 1 hour. Each well then was washed with PBS and then 150 µl of PBS containing 6×10⁷ resting or activated platelets were added to each well and the plate was incubated for 1 hour. Plates were centrifuged (300×g for 7 minutes) and incubated a further 30 minutes at room temperature. Bound platelets were fixed by addition of 0.1% (w/v) glutaraldehyde in PBS for 2 minutes at 4° C. Each well was washed with 10 mM glycine in PBS and plates were incubated with 5% (w/v) BSA containing 0.1% (w/v) sodium azide, 10 mM glycine in PBS for 1 hour at room temperature.

After washing with culture medium (RPMI 1640 containing 5% (v/v) FCS), 1×10⁶ HL60 cells labeled with [³H] thymidine were added to each well. HL60 was maintained in RPMI 1640 medium (purchased from Irvine Scientific, Santa Ana, Calif.) supplemented with 10% FCS (Hyclone, Logan, Utah). (Radiolabeling of HL60 cells used for cell adhesion assays was performed by incubating cells with 2 µCi/ml of [³H]thymidine overnight.) After incubation for 45 minutes at room temperature, unbound cells were aspirated and wells were washed once with medium (RPMI 1640 containing 5% (v/v) FCS), bound cells were detached with 0.05% (w/v) trypsin-0.02% (w/v) EDTA (Irvine Scientific) in PBS and the levels of radioactivity in each well were determined in a liquid scintillation counter.

Results from representative experiments are presented in FIGS. 12A and 12B. For both thrombin- and PMA-stimulated platelets, HL60 cell binding was inhibited strongly by TMS and DMS, but minimally inhibited by SPN. Binding of HL60 cells to activated platelets is considered to depend solely on recognition by GMP-140 of sialosyl-Le$^x$ expressed on HL60 cells since the binding was inhibited specifically by liposomes containing sialosyl-Le$^x$ but not by liposome containing other glycosphingolipids.

EXAMPLE 4

Human neutrophils were obtained from normal male adults. Heparinized peripheral blood was mixed gently with an equal amount of 1% dextran solution in PBS in a 60 ml injection syringe. The mixture was allowed to sit vertically for 60 to 90 minutes at 37° C. The upper phase, which is rich in white blood cells, was mounted gently on the same volume of Ficoll-Paque (Pharmacia LKB, Uppsala, Sweden) in Falcon 2095 plastic test tubes (Becton Dickinson Labware, Lincoln Park, N.J.). Centrifugation at 450 g for 30 min at 4° C. brought the neutrophils to the bottom of the tubes. The upper phase and interface, which contains lymphocytes, were removed carefully by aspiration.

Contaminating erythrocytes were removed from the cell pellet by hypotonic lysis by resuspending the cell pellet in ice-cold distilled water for 30 sec then adding an equal volume of ice-cold 1.8% NaCl solution. After centrifugation at 80 g for 10 min, the cells were resuspended with a suitable buffer or media.

The final preparation consisted of more than 98% neutrophils, as determined by Wright-Giemsa staining. The suspension was stored at 4° C. and used within 3 hr.

EXAMPLE 5

Superoxide production by neutrophils was quantitated by monitoring superoxide-mediated reduction of cytochrome C (Clifford, supra, in which the reduction is manifest as an increase in absorbance at 550 nm at an extinction coefficient of 21000/M/cm). Measurements were carried out with a Beckman DU-50 spectrophotometer at 37° C. using ≈1×10⁶ neutrophils per ml. The cells were allowed to equilibrate for 10 min with TMS, or other effectors, prior to addition of 1 µM of PMA.

TMS had a profound effect on neutrophil superoxide production.

EXAMPLE 6

O$_2$ consumption was measured using a Clark-type electrode with a Y.S.I. model P300 biological oxygen monitor and a micro oxygen chamber assembly (Y.S.I. Inc., Yellow Springs, Ohio). Assays were performed at 37° C. with ≈6×10⁶ neutrophils per ml in a total volume of 600 µl. The cell suspensions, in Eppendorf test tubes, were warmed at 37° C. for several minutes before being applied to the microchamber. Effectors were injected carefully using a Hamilton syringe and stirred well with a microstirrer at a speed of ≈240 rpm. The cell suspensions were pre-incubated with effectors for 5 min prior to addition of PMA to a final concentration of 1.0 µM.

TMS had a noted effect on neutrophil $O_2$ consumption.

EXAMPLE 7

Freshly purified neutrophils (≈8×10$^7$ cells) were pre-incubated at 37° C. with 2 mCi of $Na_2H[^{32}P]O_4$ in a buffer containing 0.1% lipid-free BSA-HEPES (10 mM pH 7.4, 136 mM NaCl, 4.9 mM KCl, 5.6 mM glucose and 0.33 mM $CaCl_2$) for 60 min in a shaking waterbath. Excess unbound components were removed by centrifugation and the pellets were resuspended in the same buffer, repeating twice. The cells then were divided into 7 treatment groups, each containing ≈1×10$^7$ cells in a total volume of 0.4 ml. TMS, SPN or DMS was added to a suspension and incubated at 37° C. for 10 min, followed by addition of PMA to a final concentration of 1.5 µM. Two minutes later, the reaction was terminated by adding 0.1 ml of Laemmli's sample buffer and 20 mM EDTA, followed by heating at 100° C. for 5 min. Aliquots were separated through 10% sodium dodecyl sulfate gels using known procedures. $^{32}P$ incorporation was visualized by autoradiography.

TMS had an affect on phosphorylation of specific proteins related to protein kinase C metabolism and activity.

EXAMPLE 8

Freshly purified human neutrophils (1.3×10$^8$/ml in 0.1% BSA-HEPES 10 mM buffer: pH 7.45, 136 mM NaCl, 4.9 mM KCl, 5.6 mM glucose and 0.33 mM $CaCl_2$) were incubated at 37° C. with 4 mCi of $NaH_2[^{32}P]PO_4$ for 90 min in a shaking waterbath. After incubation, the cells were washed and resuspended in the same buffer at a concentration of 1×10$^7$ cells/ml. Each suspension (1 ml) then was pretreated with TMS, SPN or DMS, or equal volume of 50% ethanol, for 10 min at 37° C. Then keeping the same temperature, fMLP was added to a final concentration of 1.0 µM. Two minutes later, the reaction was terminated by adding 3.75 ml of chloroform/methanol (1:2) to each cell suspension, followed by sonication for 15 min. An additional 1.25 ml of chloroform, 1.25 ml of water and 50 µl of acetone were added and the total mixture was mixed and left overnight.

Following centrifugation of the mixture, the phospholipids were extracted by Folch's partition method, taking the lower phase from the cell lysate. After evaporation of the lower phase, ≈10000 cpm of phosphate compounds were mounted on a Whatman HP-KF (Whatman, Maidstone, England) silica gel TLC plate, previously impregnated with methanol/water (2:3) containing 1% potassium peroxalate (Sigma, St. Louis, Mo.). The TLC plate was developed with control phospholipids, in a solvent comprising chloroform/methanol/4M NaOH at a ratio of 45:35:10 and containing 0.1% CDTA (trans-1,2-diaminocyclohexane-N,N,N',N'-tetraacetic acid) for 65 min at 37° C. The bands were identified by staining the control phospholipids with primuline and visualization under ultraviolet light. Autoradiography was performed with Kodak diagnostic film GBX-2 (Rochester N.Y.) by exposing overnight at 37° C.

TMS suppressed fMLP induced phosphorylation of phosphotidyl inositols.

EXAMPLE 9

Phagokinetic activity was observed by tracing tracks of neutrophils moving on a glass substrate covered with gold colloid particles. The technique was described originally by Albrecht-Buehler, supra, using 3T3 and other cell lines. Briefly, 22×22 mm square glass coverslips (Corning Glass Works, Corning, N.Y.) were dipped for 1 min into 1% BSA prepared in Milli Q water. The BSA solution was prepared fresh each day and passed through 0.20 µm Nalgene filters (Nalgene Labware Division, Rochester, N.Y.).

The coverslip then was drained by touching a Kim-wipe paper towel to its edge, dipped into 100% ethanol and rapidly and completely dried in a 85° C. hot airstream. The coverslip was placed in a 3.5 cm Falcon plastic dish. Then 5.4 ml of $AuCl_4H$ and 18 ml of 36.5 mM $Na_2CO_3$ were added to 33 ml of distilled water and heated. Immediately after reaching the boiling point, 5.4 ml of 0.1% formaldehyde in water were added quickly and mixed. The suspension of gold particles forming a brownish color was distributed immediately onto the dish (2 ml each) and the coverslip was incubated for 2 hr at 37° C.

Particle-coated coverslips were washed in PBS, then twice in RPMI 1640 and finally put in another 3.5 cm Falcon plastic dish containing 2 ml of RPMI 1640 with glutamate and pyruvate. The coverslips were stored at 4° C. and used within 24 hr after preparation.

The freshly-purified neutrophils (1×10$^4$ cells/plate) were added onto the colloid-coated coverslip. TMS and other effectors were added into the medium on the plate. As a control, the solvent of the effectors (50% ethanol) was added at an equal amount. At that concentration (0.1%), ethanol brought no significant effect on neutrophil activities. To observe cell recovery from exposure to the effectors, neutrophils (2×10$^5$ cells/ml) were pre-incubated at 37° C. with 12 µM of TMS, SPN and DMS, then distributed to the dish dropwise, diluting the effectors 200-fold. Incubation was conducted under 5% $CO_2$ at 37° C. for 2 hr and terminated by adding 200 µl of 10% formaldehyde. Microscopic examination of each plate was performed with a Nikon microscope, connected to a Polaroid camera for recordings. Phagokinetic activity was measured by tracing the track of a neutrophil. The track was recorded with photographs, then the area was measured by cutting and weighing there swept area.

TMS inhibited neutrophil migration without an adverse effect on cell viability.

EXAMPLE 10

HUVEC's and culture media were purchased from Cell Systems (Kirkland, Wash.). The cells were maintained and cultured as described in Luscinskas et al., supra, with some modifications. Briefly, HUVEC's were maintained in 10 ml tissue culture flasks on a collagen type I bed obtained from rat tail (Upstate Biotechnology Inc, Lake Placid, N.Y.) with CS-complete medium, CS-growth factor and CS-AF-1 (Cell Systems). Cells became confluent within 2 to 4 days when incubated in 5% $CO_2$ at 37° C.

For the transmigration assay, thick gels were formed in 24-well tissue culture plates. Preparation of the gel solution was carried out at 4° C. Eight parts of collagen solution (Vitrogen 100, from bovine tendon which contained less than 5 ng/ml endotoxin; Celtrix Labs, Palo Alto, Calif.), one part of 10×RPMI and one part of alkaline solution (2.2 g $NaHCO_3$ in 100 ml of 0.05N NaOH and 200 mM HEPES)

were mixed gently and distributed at 0.7 ml/well. The solution was left for 4 hr at 37° C. to eliminate air bubbles, then allowed to gel in a 37° C. oven for 3 hr. The wells were washed with 1.0 ml of CS-complete medium with attachment factors at least 4 times and every 3 to 6 hr during further incubation at 37° C. in 5% $CO_2$.

HUVEC's at a passage level of less than 3 were detached from 10 ml tissue culture flasks with 3 ml of Trypsin-EDTA at 37° C. for 30 to 60 sec. Immediately, 3 ml of M199 with 20% heat-inactivated FCS was added. Cells were collected by centrifugation. The pellet was resuspended in 10 ml of CS-complete medium with attachment factors. Homogeneous cell suspensions were plated at 0.7 ml to each well and the plates were incubated for 3 hr at 37° C. The supernatant, which contains dead cells, was aspirated carefully and fresh complete medium with attachment factors was added. Under those conditions, the HUVEC's formed confluent monolayers in which intracellular junctions consistently showed silver-staining within 24 hr after plating and the cells retained that property after a day in culture.

The HUVEC monolayer in 24-well tissue culture plates were washed with M199 without FCS, then incubated with 1 ml/well of IL-1β (Boehringer Mannheim Biochemical Products, Indianapolis, Ind.) dissolved in M199 with 1% heat-inactivated FCS (HIFCS) at 10 U/ml. The plates were incubated at 37° C., 5% $CO_2$ for 4 hr then washed gently with 1 ml of M199. The purified neutrophil suspension ($1.5 \times 10^6$ cells/ml) in M199 containing 1% HIFCS was pre-incubated with TMS, or other effectors, for 10 min at 37° C. After aspirating the media in the well, 0.5 ml of the neutrophil suspension were added onto the HUVEC monolayer. The tissue culture plate was incubated for 90 min at 37° C.

The culture was terminated by gently aspirating the cell suspension, adding 1 ml of 10% formaldehyde in PBS and stored at 4° C. overnight for fixation. The edge of the collagen bed was cut with a small spatula along the wall 2 hr before removal from the well. The collagen bed, which has HUVEC's on the surface and transmigrated neutrophils within was embedded in paraffin, sectioned and followed by staining with hematoxylin-eosin for microscopic examination.

TMS affected neutrophil migration without effecting cell viability.

EXAMPLE 11

Liposomes were prepared as described in Park & Huang, Biochem; Biophys. Acta, 1166, 105, 1993. A mixture of egg phosphatidyl choline (Avanti Polar Lipids, Birmingham, Ala.) (PC)/cholesterol (Sigma Chemical, St. Louis, Mo.) (chol)/TMS (4.5:4.5:1, molar ratio) was dried under an $N_2$ stream and vacuum-desiccated overnight. The lipid mixture was hydrated with phosphate-buffered saline (PBS) or Eagle's medium. Liposomes were prepared by sonication or extrusion. For example, the lipid mixture was hydrated and sonicated with a bath type sonicator (Laboratory Supply Co., Hickville, N.Y.) twice for 10 minutes with a 30 minute interval, which gave small unilamellar vesicles. Alternatively, the fully hydrated lipid mixture (45° C.) was passed through a series of paired polycarbonate membrane filters (0.6 μm, 0.4 μm and 0.2 m pore size; five times each) using an extruder (Lipex Biomembrane, Vancouver, Canada) connected to a temperature control unit (Lauda-Brinkmann Instrument Co., Westbury, N.J. That procedure gave homogenous liposomal vesicles.

EXAMPLE 12

BL6 melanoma cells (obtained from Dr. I. J. Fidler of M.D. Anderson Cancer Center, Houston, Tex. and cultured in Eagle's MEM supplemented with 5% fetal calf serum, 1% nonessential amino acids, 2 mM glutamine, 1.5% vitamin solution and 1% sodium pyruvate) were injected i.v. (200 μl, $4 \times 10^4$ cells) into C57BL6 mice 7–10 weeks of age, ~20 g body weight, via a tail vein, followed after 15 min. by the first i.v. injection of liposomal TMS. The second and third i.v. injections of liposomal TMS were given on days 5 and 10. Mice were sacrificed on day 18 and colony numbers in lung were counted under a dissecting microscope.

Liposomal TMS reduced lung colonization.

For studies on spontaneous metastasis, BL6 cells (50 μl, $2 \times 10^5$ cells) were injected s.c. into a mouse footpad and liposomal TMS was injected i.v. on days 5, 10, 15, 20, 25 and 30. Primary tumors were excised on day 21 and tumor weight was measured. Mice were sacrificed and lung colonization was assessed.

Liposomal TMS suppressed tumor growth.

Liposomal TMS also inhibited lung colonization.

EXAMPLE 13

Biodistribution assays were performed as previously described in Park & Huang, supra, with minor modifications. Liposomal TMS containing a trace amount of [$^{111}$In] diethylenetriamine pentaacetic acid distearylamine complex (obtained from Dr. L. Huang, Dept. Pharm., Univ. Pittsburgh, Pittsburgh, Pa., prepared by mixing 1 μl of [$^{111}$In] $Cl_3$.HCl with 0.6 ml of 1 mM DTPA-SA in ethanol at 80° C. with sonication for a few seconds) (DTPA-SA), which is a non-metabolizable and nonexchangeable marker of liposomes (Holmberg et al., Biochem. Biophys. Res. Comm., 165, 1272, 1989), was prepared by the extrusion method. [$^{111}$In]liposomal TMS (0.2 ml) was injected i.v. into C57BL/6 mice, 7–10 weeks old, ≈20 g body weight which were sacrificed 5 minutes and 1 hour post injection. Radioactivity of organs containing $^{111}$In was counted with a γ-counter. Weight of mouse blood was assumed to be 7.3% of body weight. Blood content of other organs was corrected as taught in Liu et al., Biochem. Biophys. Acta, 1066, 159, 1991.

All references cited herein are herein incorporated by reference.

While the invention has been described in detail and with reference to certain embodiments thereof, it would be apparent to one skilled in the art that various changes and modifications can be made without departing from the spirit and scope thereof.

What is claimed is:

1. N,N,N-Trimethylsphingosine contained within a liposome.

2. The trimethylsphingosine liposome of claim 1 further comprising within said liposome a pharmaceutically acceptable carrier, diluent or excipient.

3. A pharmaceutical composition comprising a cell proliferation inhibiting amount of the trimethylsphingosine liposome of claim 1 and a pharmaceutically acceptable carrier, diluent or excipient.

4. A pharmaceutical composition comprising a platelet aggregation inhibiting amount of the trimethylsphingosine liposome of claim 1 and a pharmaceutically acceptable carrier, diluent or excipient.

* * * * *